(12) United States Patent
Silver et al.

(10) Patent No.: US 12,178,579 B1
(45) Date of Patent: Dec. 31, 2024

(54) SENSOR FOR MONITORING POSTURE

(71) Applicant: MYOMONITOR LLC, Chapel Hill, NC (US)

(72) Inventors: William P. Silver, Chapel Hill, NC (US); Stephen Clay Trotter, Cary, NC (US); Richard K. Woodard, Charlotte, NC (US); Benjamin Gatti, Lake Park, NC (US); Emily Caldwell, Charlotte, NC (US)

(73) Assignee: MYOMONITOR LLC, Chapel Hill, NC (US)

( * ) Notice: Subject to any disclaimer, the term of this patent is extended or adjusted under 35 U.S.C. 154(b) by 434 days.

(21) Appl. No.: 17/141,208

(22) Filed: Jan. 4, 2021

Related U.S. Application Data

(60) Provisional application No. 62/956,641, filed on Jan. 3, 2020.

(51) Int. Cl.
| | |
|---|---|
| *A61B 5/256* | (2021.01) |
| *A61B 5/00* | (2006.01) |
| *A61B 5/11* | (2006.01) |
| *A61B 5/296* | (2021.01) |
| *A61B 5/397* | (2021.01) |

(52) U.S. Cl.
CPC ............ *A61B 5/256* (2021.01); *A61B 5/1116* (2013.01); *A61B 5/296* (2021.01); *A61B 5/397* (2021.01); *A61B 5/6804* (2013.01); *A61B 5/7405* (2013.01); *A61B 5/7455* (2013.01); *A61B 5/746* (2013.01); *A61B 2560/0214* (2013.01); *A61B 2562/0209* (2013.01); *A61B 2562/043* (2013.01); *A61B 2562/227* (2013.01)

(58) Field of Classification Search
CPC ....... A61B 5/256; A61B 5/1116; A61B 5/296; A61B 5/397; A61B 5/6804; A61B 5/7405; A61B 5/7455; A61B 5/746; A61B 2560/0214; A61B 2562/0209; A61B 2562/043; A61B 2562/227
See application file for complete search history.

(56) References Cited

U.S. PATENT DOCUMENTS

| | | | | |
|---|---|---|---|---|
| 2014/0364703 | A1* | 12/2014 | Kim ..................... | A61B 5/6824 600/301 |
| 2015/0374280 | A1* | 12/2015 | Tomasi ................. | A61B 5/486 600/409 |
| 2016/0022210 | A1* | 1/2016 | Nuovo ................. | A61B 5/6831 600/301 |
| 2022/0361815 | A1* | 11/2022 | Kuwabara ............... | A61B 5/11 |

\* cited by examiner

*Primary Examiner* — Alex M Valvis
*Assistant Examiner* — Nidhi N Patel
(74) *Attorney, Agent, or Firm* — TILLMAN WRIGHT, PLLC; Chad D. Tillman

(57) ABSTRACT

Wearable sensors and uses thereof are disclosed. Preferred sensors include surface EMG electrodes for measuring electrical muscle activity, by which muscle contraction is measured. Such muscle contraction can be used to determine a person's posture, especially when the contraction being measured is that of core muscles. An alert preferably is provided to a person in real time when an incorrect posture is detected. By providing such biofeedback, a person is trained in maintaining a good posture. Such posture training is believed to heal alleviate or even present lower back pain. Wearable sensors of the invention also can be used to measure contraction in muscles during exercise, including running and strength training, to gain information for use in improving such activities.

13 Claims, 36 Drawing Sheets

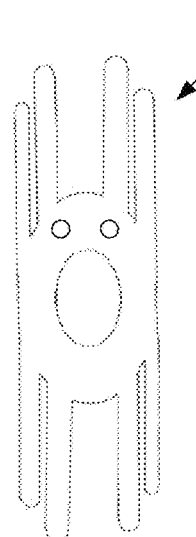
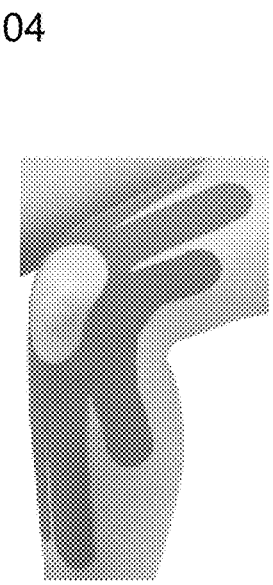
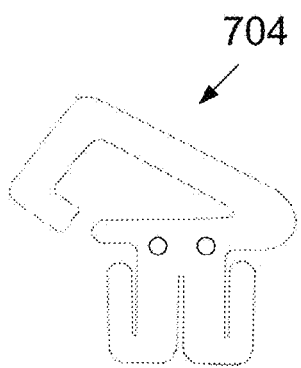
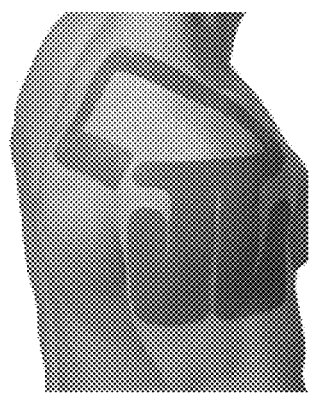
Knee
FIG. 35   FIG. 36   FIG. 37   FIG. 38
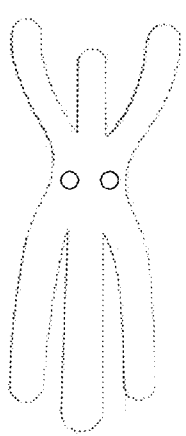
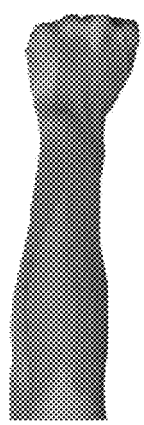
Arm
FIG. 39   FIG. 40   FIG. 41

Above 80% power

20%-80% power

Under 20% power

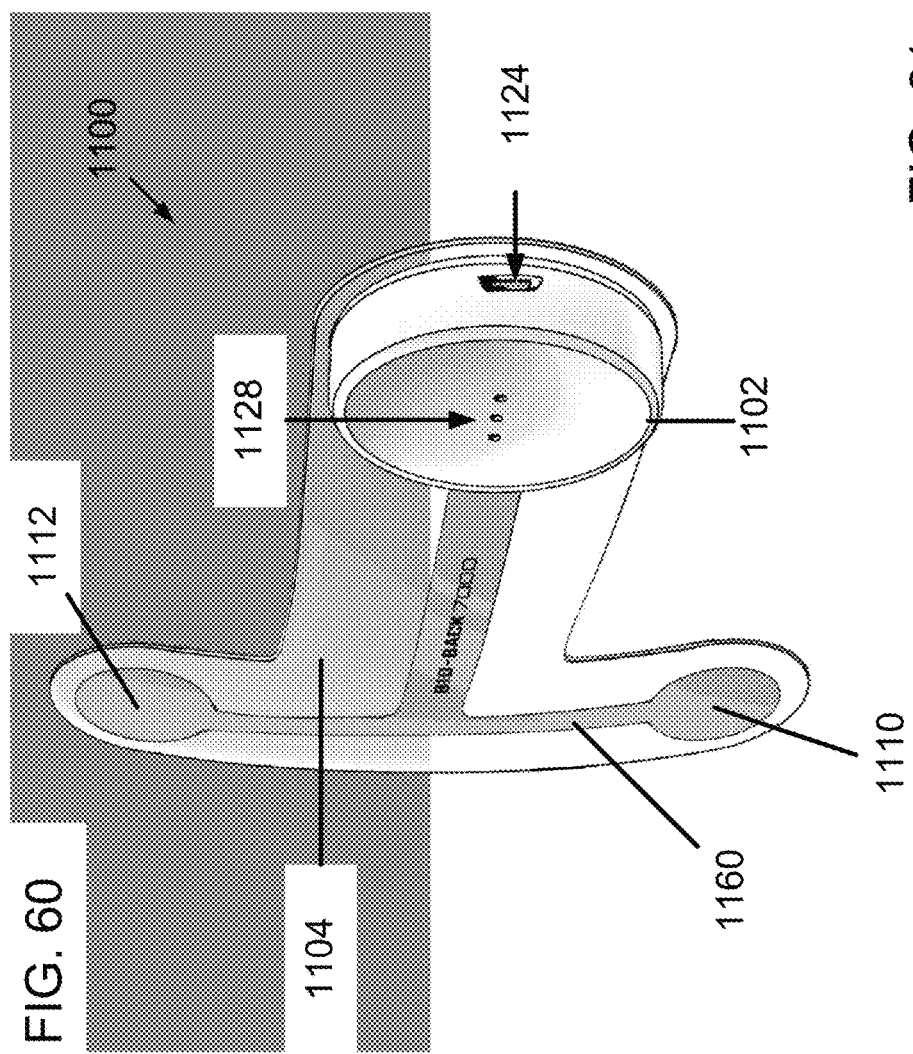
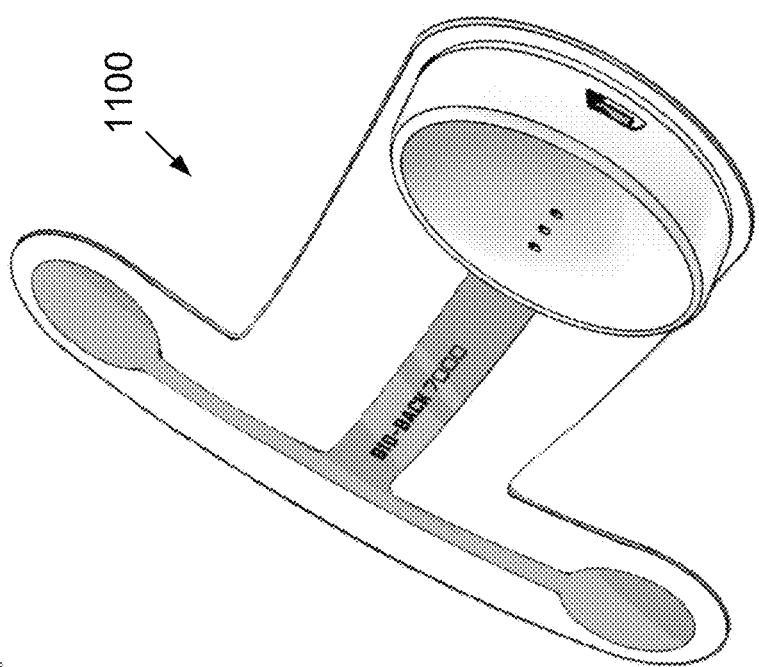
FIG. 60
FIG. 61

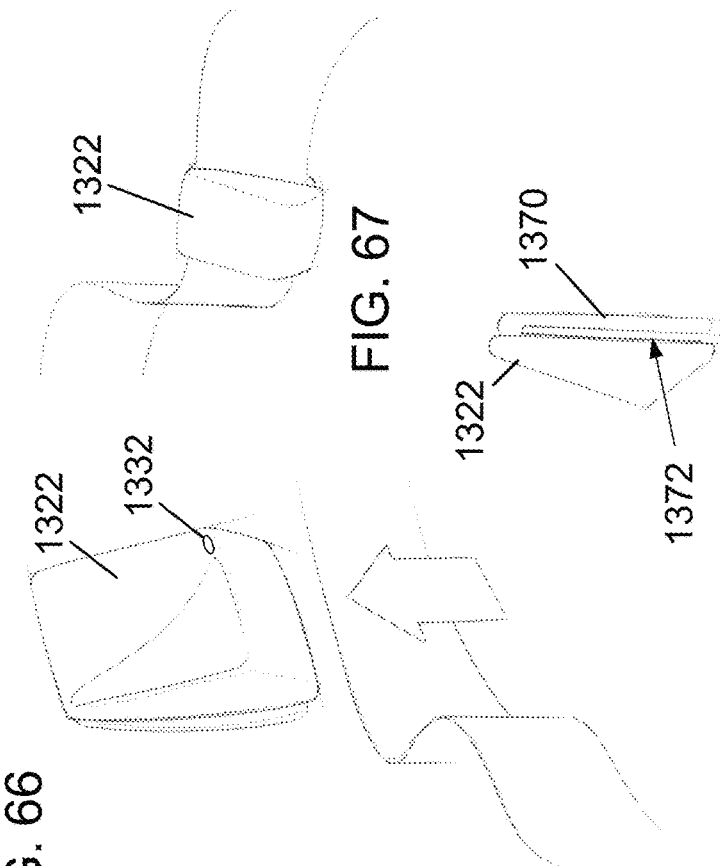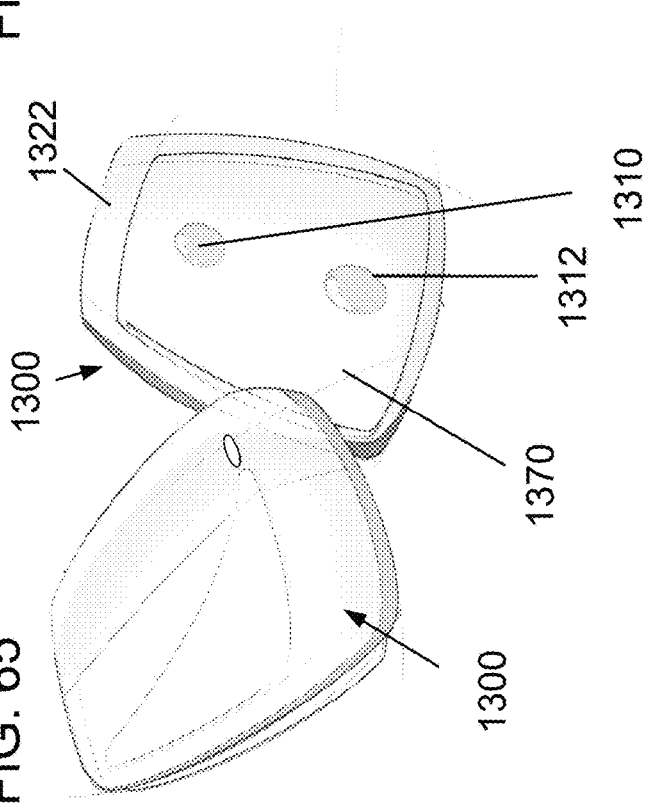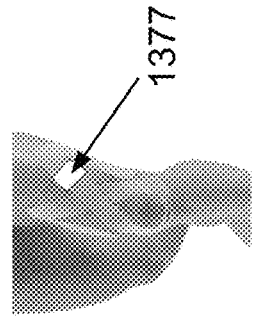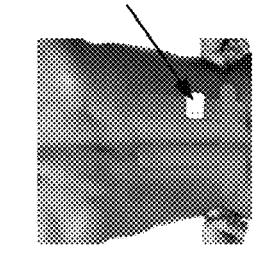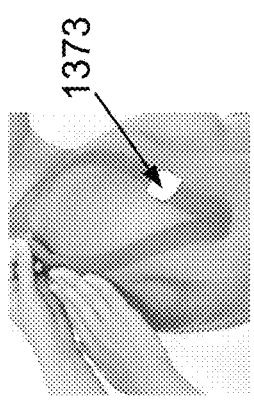

SENSOR FOR MONITORING POSTURE

COPYRIGHT STATEMENT

Any new and original work of authorship in this document—including any source code—is subject to copyright protection under the copyright laws of the United States and other countries. Reproduction by anyone of this document as it appears in official governmental records is permitted, but otherwise all other copyright rights whatsoever are reserved.

COMPUTER PROGRAM LISTING

Submitted concurrently herewith via the USPTO's electronic filing system, and incorporated herein by reference, are computer program files including instructions, routines, and/or other contents of several computer programs. A table setting forth the name and size of files included in the computer program listing is included below.

| File Name | Creation Date | File Size (bytes) |
| --- | --- | --- |
| ascify.txt | Dec. 27, 2019 15:56 | 37,473 |
| readme.txt | Dec. 27, 2019 15:56 | 2,594 |
| emg.txt | Dec. 27, 2019 15:48 | 3,064,270 |

One of these files, "readme.txt", contains instructions for extracting information from "emg.txt". "emg.txt" represents a compressed binary file that has been converted to ascii format. This file can be converted back to a compressed.zip archive utilizing an assembly conversion program source code for which is contained in "ascify.txt". The readme file includes instructions for compiling and running this conversion program, and instructions for converting the other text files to a compressed, binary file. This compressed, binary file includes eDrawings files for computer models illustrating aspects and features in accordance with one or more preferred embodiments of the invention.

BACKGROUND OF THE INVENTION

The present invention generally relates to wearable sensors and uses thereof.

In particular, it is believed that lower back pain affects about twenty percent of the population each year, and that eighty percent of people are affected at some point during their lifetime. Strengthening core muscles including the abdominal musculature is a common physical therapy technique used to treat or prevent lower back pain. Biofeedback can be used to train patients to engage or contract specific muscle groups, such as the abdominal muscles, and electromyogram (EMG) devices can be and are used to measure muscle contraction. An embodiment in accordance with one or more aspects and features of the invention is believed to provide an improved, wearable EMG device that provides biofeedback for posture training persons in better back health for purposes of reducing or even preventing lower back pain. Other benefits are also believed to be provided by other embodiments in accordance with one or more aspects and features of the invention.

SUMMARY OF THE INVENTION

The present invention includes many aspects and features. Moreover, while many aspects and features relate to, and are described in, the context of posture training, the present invention is not limited to such use, as will become apparent from the following summaries and detailed descriptions of aspects, features, and one or more embodiments of the present invention.

In an aspect, a sensor is configured to be worn by a person and vibrate when incorrect posture of the person is detected.

In a feature, the sensor is configured to monitor core muscles of the person by which an incorrect posture of the person is detected.

In a feature, the sensor comprises a component for alerting a person wearing the sensor. The component may comprise a vibration mechanism, a speaker for auditory alerts, or both.

Another aspect comprises a method of using a sensor of any of the foregoing sensor claims to monitor a person's posture.

Another aspect comprises a method of using a sensor of any of the foregoing sensor claims to monitor a person's posture and providing feedback to the person.

In another aspect, a sensor module comprises: (a) a casing; (b) circuitry; (c) a microcontroller; (d) a transceiver; (e) a power source; and (f) a component for alerting a person wearing the sensor module. The casing contains the circuitry, microcontroller, and transceiver.

In a feature, the power source comprises a battery.

In a feature, the power source comprises a rechargeable battery. The sensor module further preferably comprises a charging port located in a wall of the casing for charging of the rechargeable battery. Alternatively, the rechargeable battery may be wirelessly charged.

In a feature, the casing further contains the component for alerting a person wearing the sensor module. The component for alerting a person wearing the sensor module may comprise a vibration mechanism; a speaker for providing an auditory alert; or both. The casing if containing a speaker preferably includes audio openings defined in a wall thereof proximate the speaker contained therein.

Another aspect comprises a method of using a sensor module as disclosed herein to monitor a person's posture.

Another aspect comprises a method of using a sensor module as disclosed herein to monitor a person's posture and provide feedback to the person in posture training of the person.

In another aspect, a fabric article having electrodes and configured to removable receive a sensor module comprises: (a) a top layer; and (b) a bottom layer. The electrodes extend through at least the bottom layer; and a sensor-module attachment structure extends through and away from the top layer and is secured by the top and bottom layers.

In a feature, a bracket secures the sensor-module attachment structure to the electrodes. The bracket preferably is sandwiched between the top layer and the bottom layer.

Another aspect comprises a fabric article as disclosed herein.

In another aspect, a sensor comprises a sensor module as disclosed herein and a fabric article as disclosed herein.

In yet another aspect, a method of attaching a sensor comprises the steps of: (a) donning a fabric article having electrodes and configured to removably receive a senor module, wherein the fabric article at least partially covers an area of the person's body to be monitored; (b) attaching a sensor module to the fabric article such that the electrodes are in electronic communication with the sensor module; (c) monitoring the area of the person's body using the sensor module; and (d) removing the sensor module from the fabric article for later reuse of the sensor module.

In a feature, the method further comprises disposing of the fabric article after removing the sensor module.

In a feature, the fabric article comprises kinesiology tape and the donning step comprises arranging the kinesiology tape in a taping pattern proximate one or more muscles to be targeted. The one or more muscles to be monitored may comprise core muscles, and the area of the body to be monitored comprises the abdomen.

In a feature, the fabric article has a T-shaped footprint.

In a feature, the fabric article has a rounded square footprint.

Another aspect comprises a method of monitoring a person's posture and providing feedback to the person as disclosed herein. The feedback preferably is given in real time as the posture is being monitored, and vibrations alerting the person of an incorrect posture, auditory alerts indicating an incorrect posture, or both. Illumination of an indicator, such as an LED light, also may be utilized to provide such feedback.

In a feature of one or more of the foregoing method aspects, monitoring of a person's posture comprises measuring muscle contraction of core muscles that contribute to or accomplish proper posture by the person.

In a feature of one or more of the foregoing apparatus aspects, the apparatus is configured to measure muscle contraction of core muscles that contribute to or accomplish proper posture by the person. Preferably such measurement is done using an EMG device or components thereof.

Other aspects comprise methods of sports monitoring and training using sensors as disclosed herein; methods of providing biofeedback for posture improvement as disclosed herein; methods of actuating a prosthetic device using a sensor as disclosed herein; and a user notification and monitoring system as disclosed herein.

Still other aspects includes sensor as disclosed herein; sensor modules as disclosed herein; sensor bases including fabric articles as disclosed herein; systems as disclosed herein; and methods as disclosed herein.

Additional aspects and features are disclosed in the program files of the computer program listing, which is incorporated herein by reference.

In addition to the aforementioned aspects and features of the present invention, it should be noted that the present invention further encompasses the various logical combinations and subcombinations of such aspects and features. Thus, for example, claims in this or a divisional or continuing patent application or applications may be separately directed to any aspect, feature, or embodiment disclosed herein, or combination thereof, without requiring any other aspect, feature, or embodiment.

BRIEF DESCRIPTION OF THE DRAWINGS

One or more preferred embodiments of the present invention now will be described in detail with reference to the accompanying drawings, wherein the same elements are referred to with the same reference numerals, and wherein.

FIG. 35 is a schematic view of a bottom of another sensor base for use proximate a knee in accordance with one or more aspects and features of the invention.

FIG. 36 is a photograph showing a kinesiology taping pattern to which the footprint of FIG. 35 corresponds.

FIG. 37 is a schematic view of another sensor base for use proximate a shoulder in accordance with one or more aspects and features of the invention.

FIG. 38 is a photograph showing a kinesiology taping pattern to which the footprint of FIG. 37 corresponds.

FIG. 39 is a schematic view of another sensor base for use proximate an arm in accordance with one or more aspects and features of the invention.

FIG. 40 is a photograph showing a kinesiology taping pattern to which the footprint of FIG. 39 corresponds.

FIG. 41 is a photograph showing a kinesiology taping pattern to which another preferred footprint corresponds in accordance with one or more aspects and features of the invention.

FIG. 60 is a perspective view of an alternative sensor in accordance with one or more aspects and features of the invention.

FIG. 61 is another perspective view of the sensor of FIG. 60.

FIG. 65 is a perspective view of the top and the bottom of an alternative sensor in accordance with one or more aspects and features of the invention.

FIG. 66 is a perspective view of the sensor of FIG. 65 being attached to a band of tape.

FIG. 67 is a perspective view of the sensor of FIG. 65 attached to a band of tape.

FIG. 68 is a side elevational view of the sensor of FIG. 65.

FIG. 69 is a perspective view illustrating attachment of the sensor of FIG. 65 to a person's shoulder.

FIG. 70 is a perspective view illustrating attachment of the sensor of FIG. 65 to a person's lower back.

FIG. 71 is a perspective view illustrating attachment of the sensor of FIG. 65 to a person's thigh.

DETAILED DESCRIPTION

Figure 1:
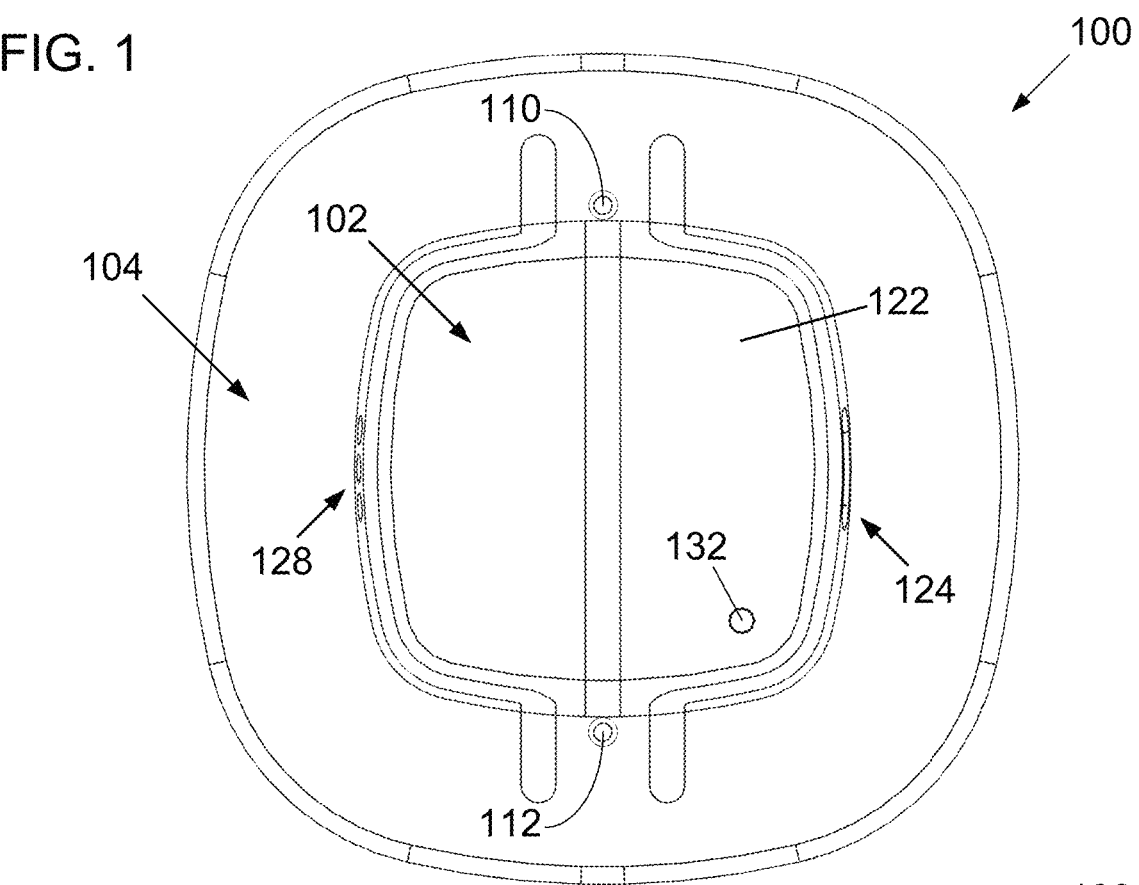
FIG. 1 is a top plan view of a sensor in accordance with one or more aspects and features of the invention.

As a preliminary matter, it will readily be understood by one having ordinary skill in the relevant art ("Ordinary Artisan") that the invention has broad utility and application. Furthermore, any embodiment discussed and identified as being "preferred" is considered to be part of a best mode contemplated for carrying out the invention. Other embodiments also may be discussed for additional illustrative purposes in providing a full and enabling disclosure of the invention. Furthermore, an embodiment of the invention may incorporate only one or a plurality of the aspects of the invention disclosed herein; only one or a plurality of the features disclosed herein; or combination thereof. As such, many embodiments are implicitly disclosed herein and fall within the scope of what is regarded as the invention.

Accordingly, while the invention is described herein in detail in relation to one or more embodiments, it is to be understood that this disclosure is illustrative and exemplary of the invention and is made merely for the purposes of providing a full and enabling disclosure of the invention. The detailed disclosure herein of one or more embodiments is not intended, nor is to be construed, to limit the scope of patent protection afforded the invention in any claim of a patent issuing here from, which scope is to be defined by the claims and the equivalents thereof. It is not intended that the scope of patent protection afforded the invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the invention. Accordingly, it is intended that the scope of patent protection afforded the invention be defined by the issued claim(s) rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term-differs in any way from any particular dictionary definition of such term, it is intended that the meaning of the term as understood by the Ordinary Artisan should prevail.

With regard solely to construction of any claim with respect to the United States, no claim element is to be interpreted under 35 U.S.C. 112(f) unless the explicit phrase "means for" or "step for" is actually used in such claim element, whereupon this statutory provision is intended to and should apply in the interpretation of such claim element. With regard to any method claim including a condition precedent step, such method requires the condition precedent to be met and the step to be performed at least once but not necessarily every time during performance of the claimed method.

Furthermore, it is important to note that, as used herein, "comprising" is open-ended insofar as that which follows such term is not exclusive. Additionally, "a" and "an" each generally denotes "at least one" but does not exclude a plurality unless the contextual use dictates otherwise. Thus, reference to "a picnic basket having an apple" is the same as "a picnic basket comprising an apple" and "a picnic basket including an apple", each of which identically describes "a picnic basket having at least one apple" as well as "a picnic basket having apples"; the picnic basket further may contain one or more other items beside an apple. In contrast, reference to "a picnic basket having a single apple" describes "a picnic basket having only one apple"; the picnic basket further may contain one or more other items beside an apple. In contrast, "a picnic basket consisting of an apple" has only a single item contained therein, i.e., one apple; the picnic basket contains no other item.

When used herein to join a list of items, "or" denotes "at least one of the items" but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers"; the picnic basket further may contain one or more other items beside cheese and crackers.

When used herein to join a list of items, "and" denotes "all of the items of the list". Thus, reference to "a picnic basket having cheese and crackers" describes "a picnic basket having cheese, wherein the picnic basket further has crackers", as well as describes "a picnic basket having crackers, wherein the picnic basket further has cheese"; the picnic basket further may contain one or more other items beside cheese and crackers.

The phrase "at least one" followed by a list of items joined by "and" denotes an item of the list but does not require every item of the list. Thus, "at least one of an apple and an orange" encompasses the following mutually exclusive scenarios: there is an apple but no orange; there is an orange but no apple; and there is both an apple and an orange. In these scenarios if there is an apple, there may be more than one apple, and if there is an orange, there may be more than one orange. Moreover, the phrase "one or more" followed by a list of items joined by "and" is the equivalent of "at least one" followed by the list of items joined by "and".

Referring now to the drawings, one or more preferred embodiments of the invention are next described. The following description of one or more preferred embodiments is merely exemplary in nature and is in no way intended to limit the invention, its implementations, or uses.

Figure 2:
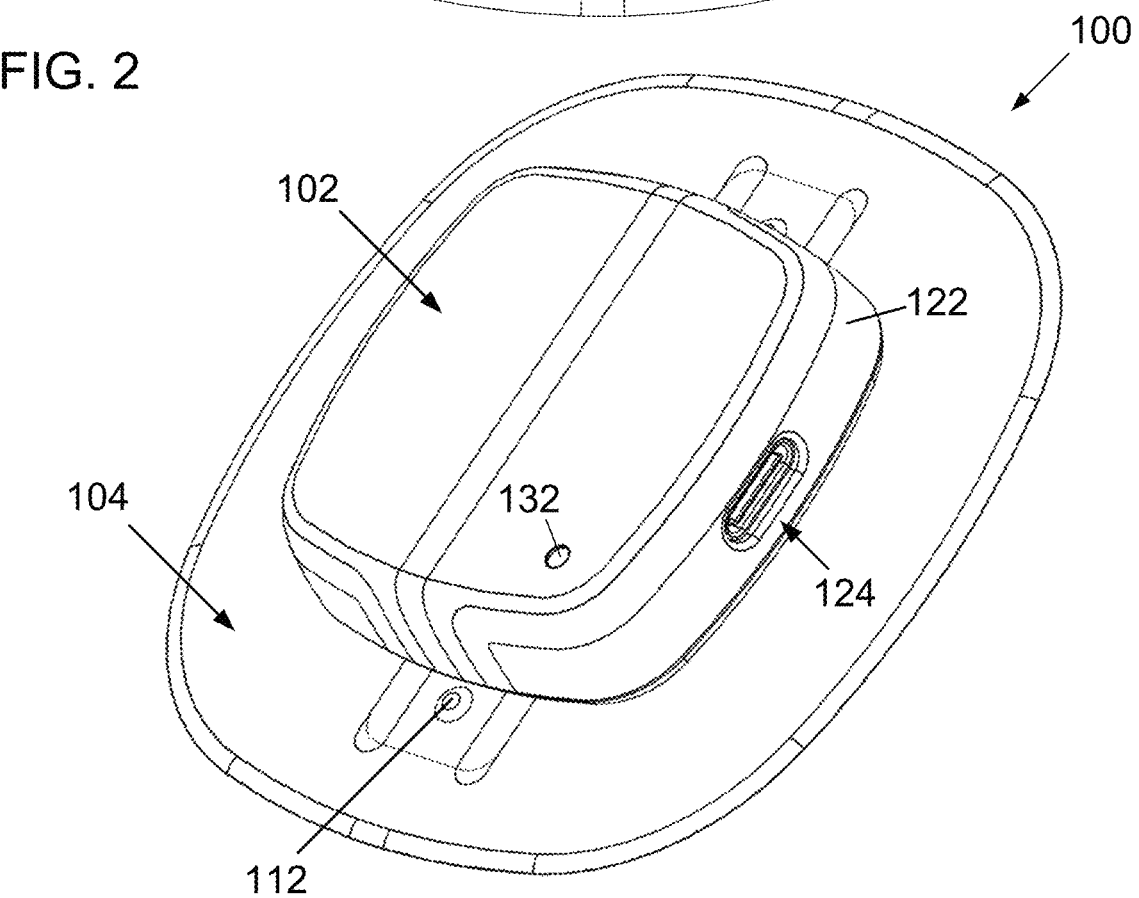
FIG. 2 is a perspective view of the sensor of FIG. 1.
Figure 2A:
FIG. 2A is a shaded version of the view of FIG. 2.
Figure 3:
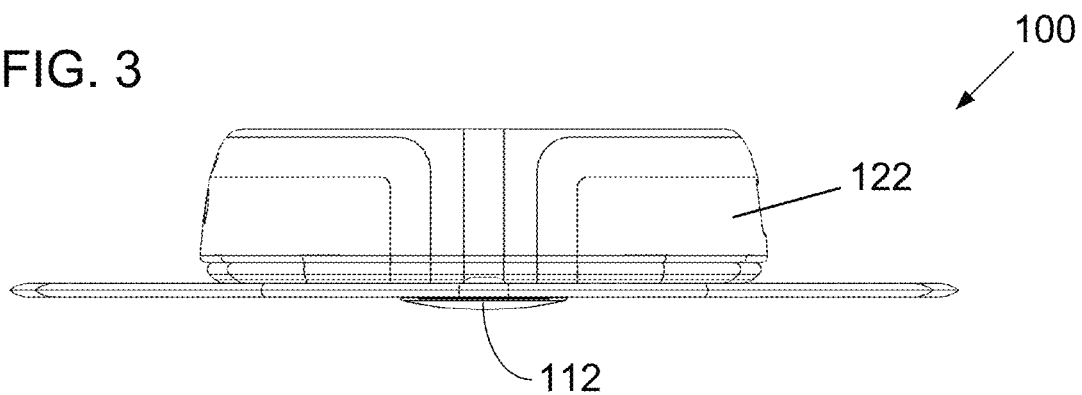
FIG. 3 is an elevational view of a first side of the sensor of FIG. 1.
Figure 4:
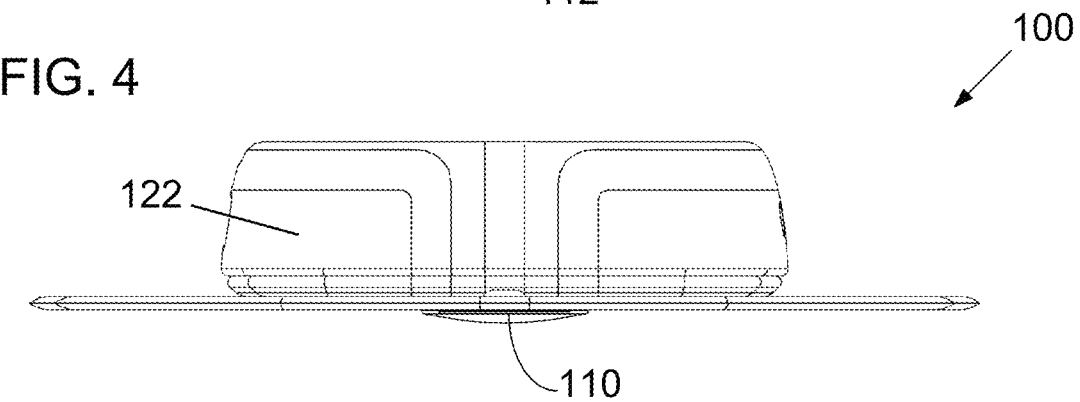
FIG. 4 is an elevational view of a second side of the sensor of FIG. 1.
Figure 5:
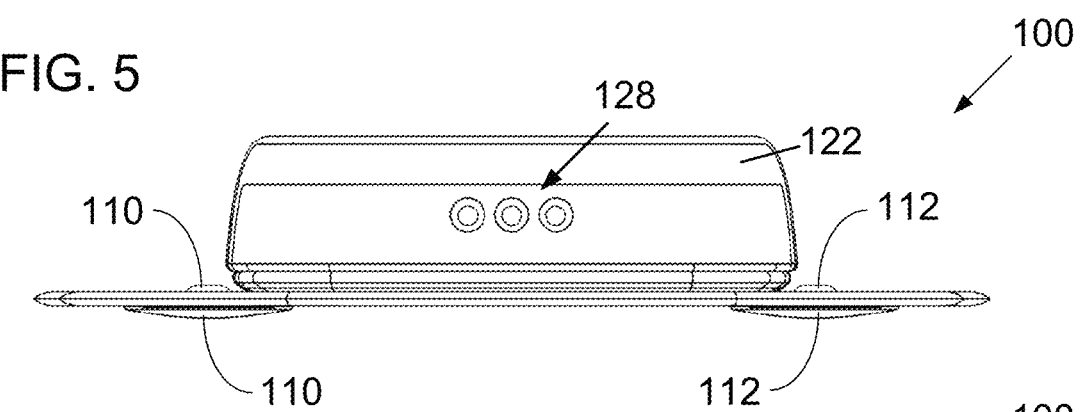
FIG. 5 is an elevational view of a front of the sensor of FIG. 1.
Figure 6:
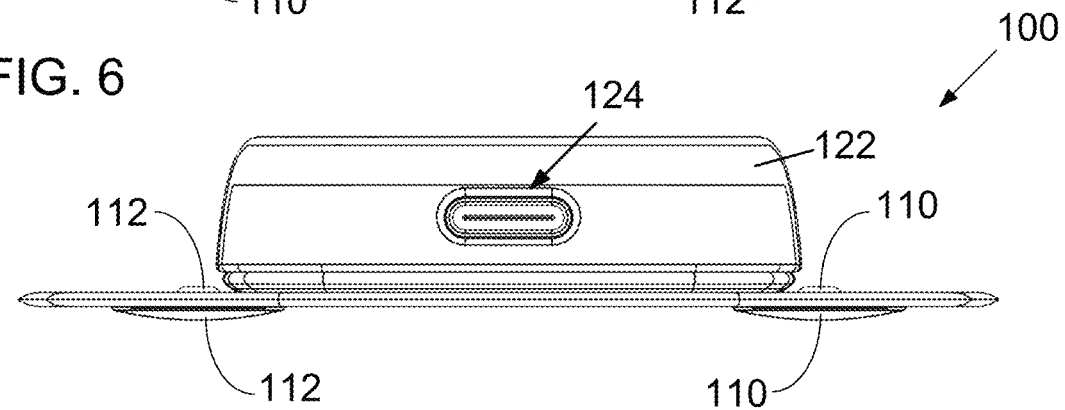
FIG. 6 is an elevational view of a back of the sensor of FIG. 1.
Figure 3A:
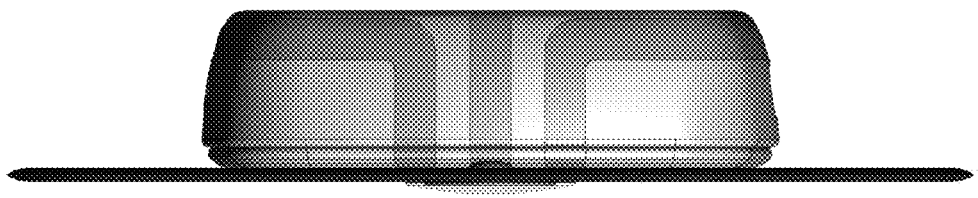
FIG. 3A is a shaded version of the view of FIG. 3.
Figure 4A:
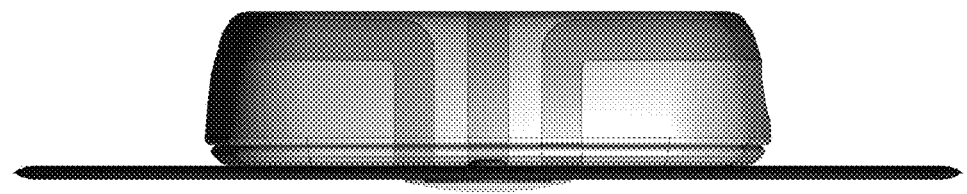
FIG. 4A is a shaded version of the view of FIG. 4.
Figure 5A:
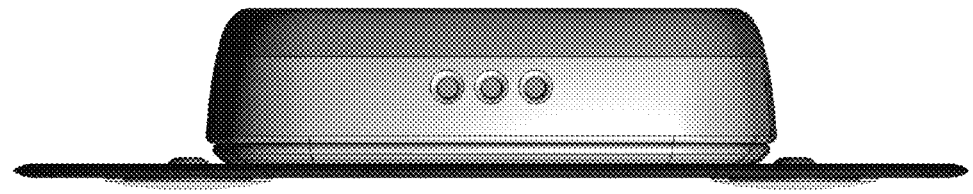
FIG. 5A is a shaded version of the view of FIG. 5.
Figure 6A:
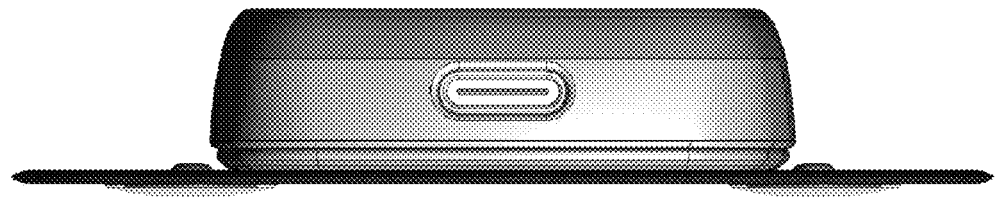
FIG. 6A is a shaded version of the view of FIG. 6.
Figure 7:
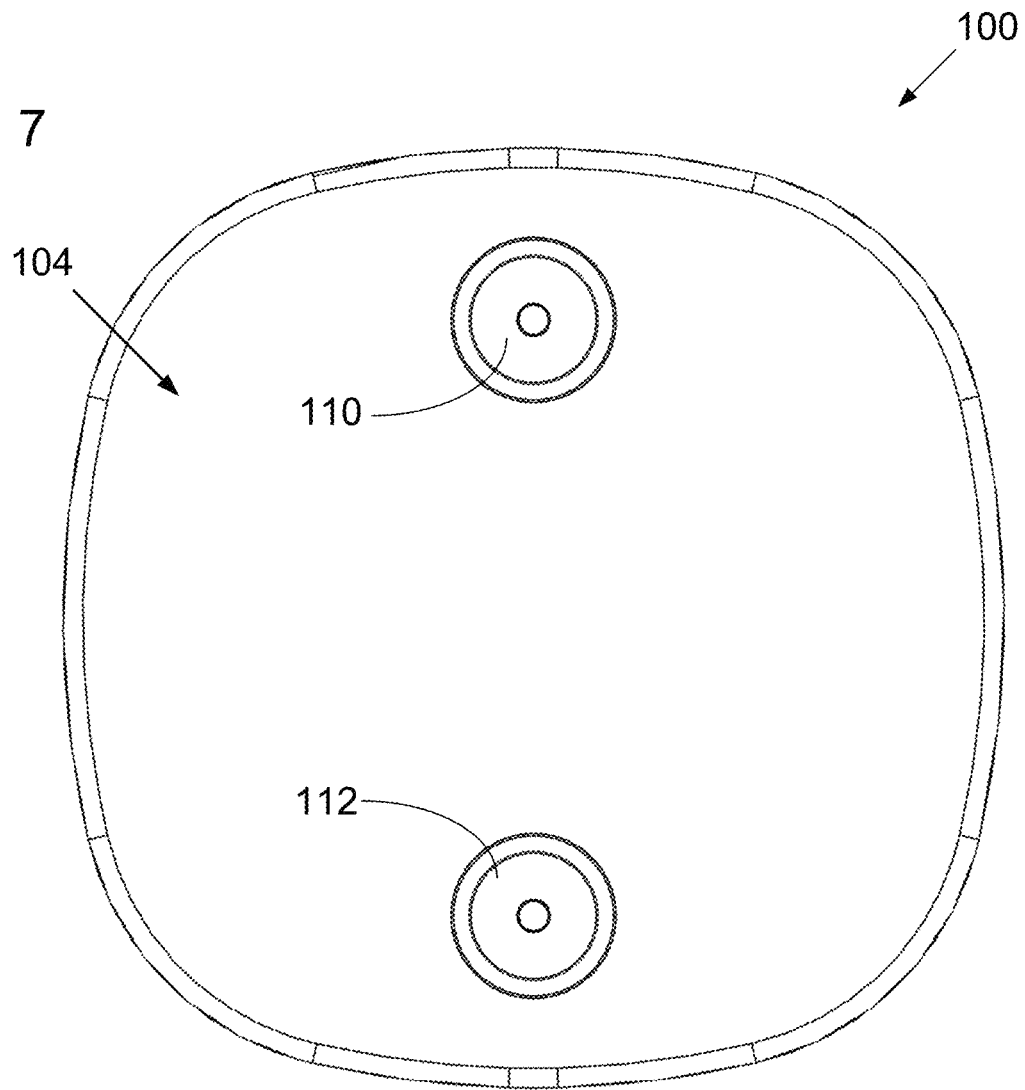
FIG. 7 is a bottom plan view of the sensor of FIG. 1.
Figure 7A:
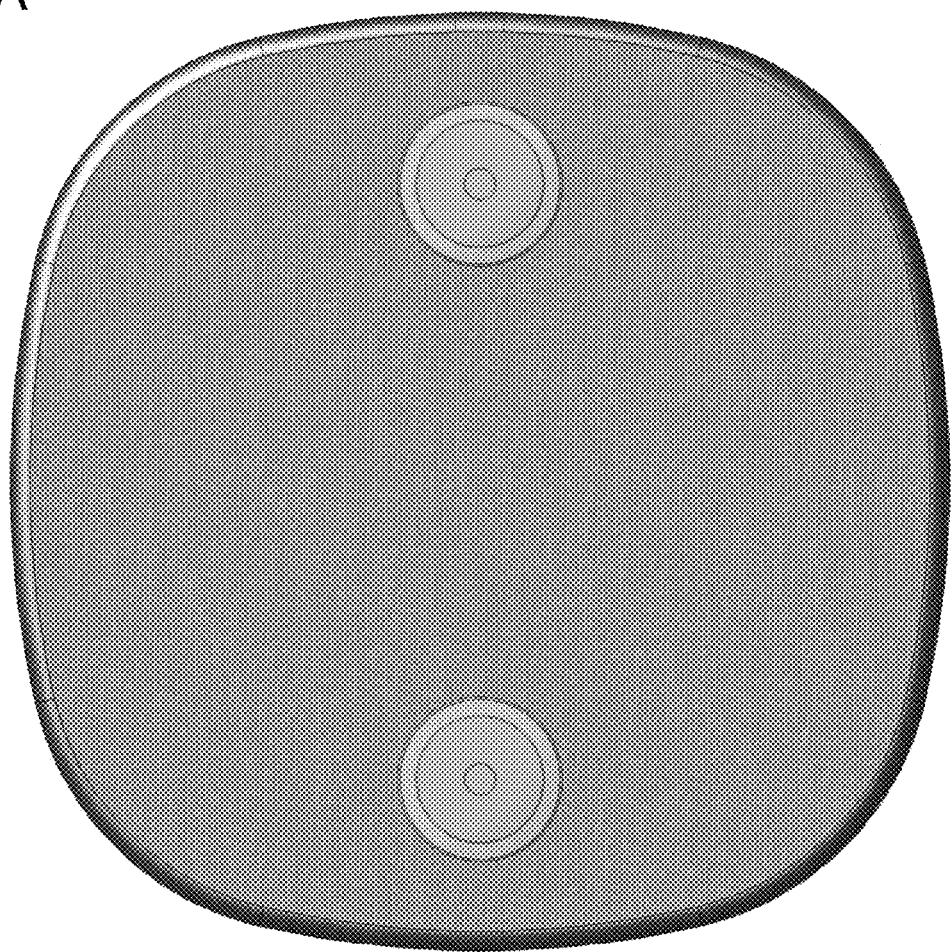
FIG. 7A is a shaded version of the view of FIG. 7.
Figure 8:
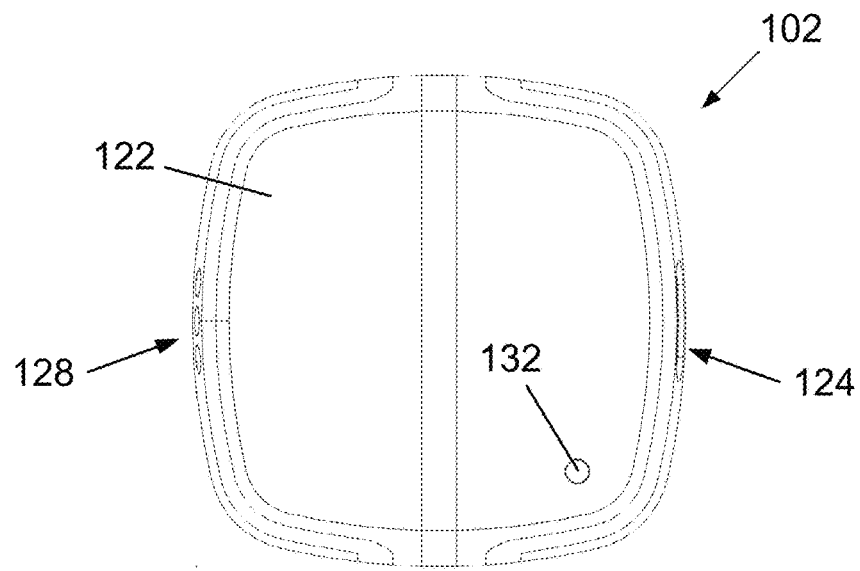
FIG. 8 is a top plan view of a sensor module of the sensor of FIG. 1.
Figure 9:
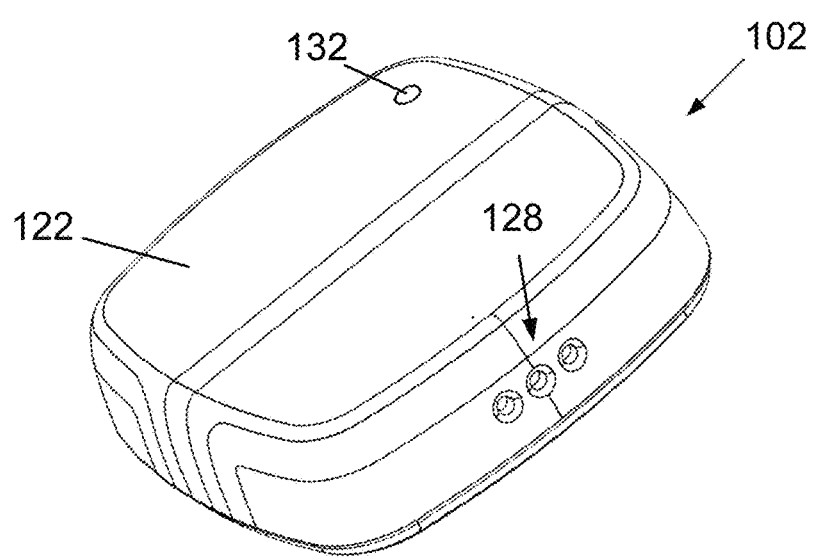
FIG. 9 is a perspective view of a top of the sensor module of FIG. 8.
Figure 10:
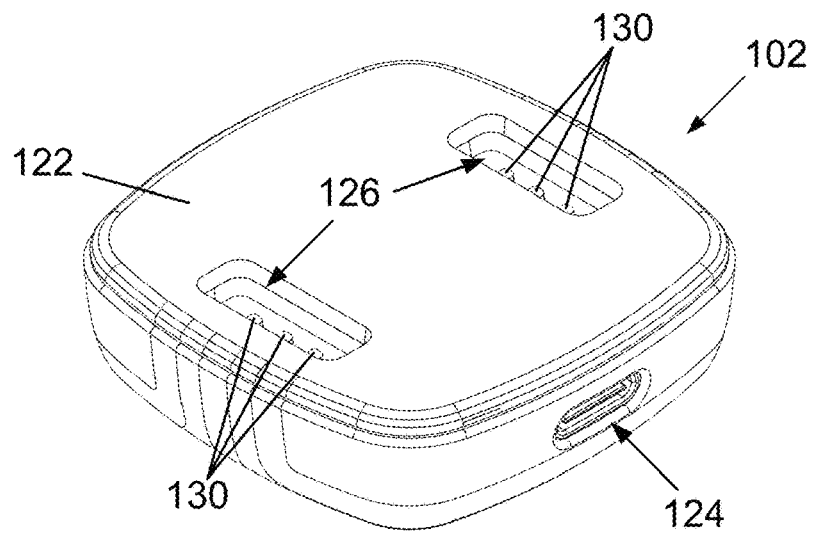
FIG. 10 is another perspective view of the bottom of the sensor module of FIG. 8.
Figure 8A:
FIG. 8A is a shaded version of the view of FIG. 8.
Figure 9A:
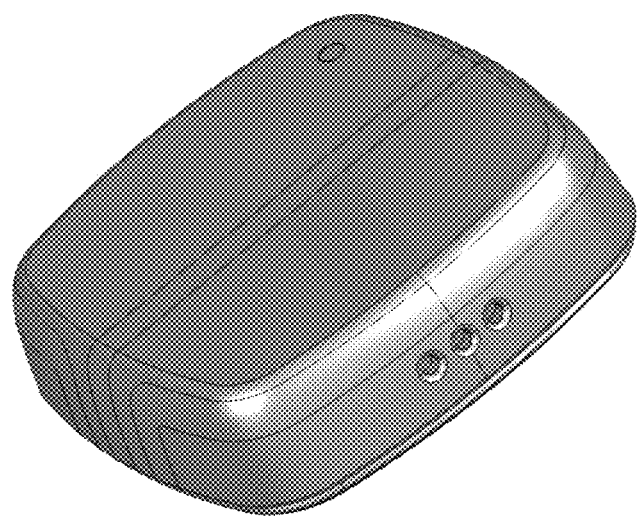
FIG. 9A is a shaded version of the view of FIG. 9.
Figure 10A:
FIG. 10A is a shaded version of the view of FIG. 10.
Figure 11:
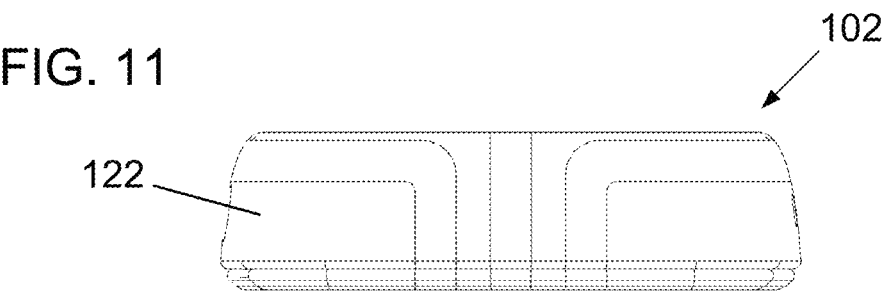
FIG. 11 is an elevational view of a first side of the sensor module of FIG. 8.
Figure 12:
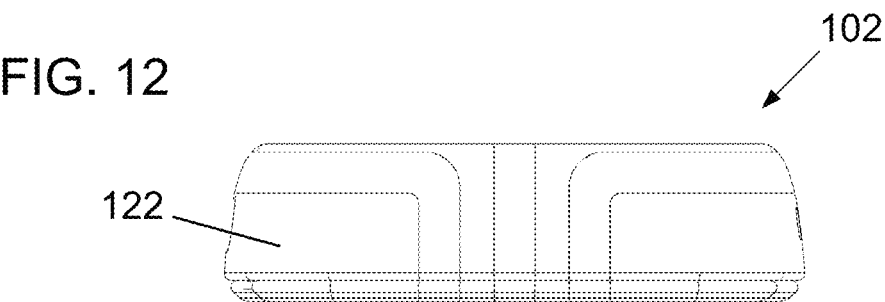
FIG. 12 is an elevational view of a second side of the sensor module of FIG. 8.
Figure 13:
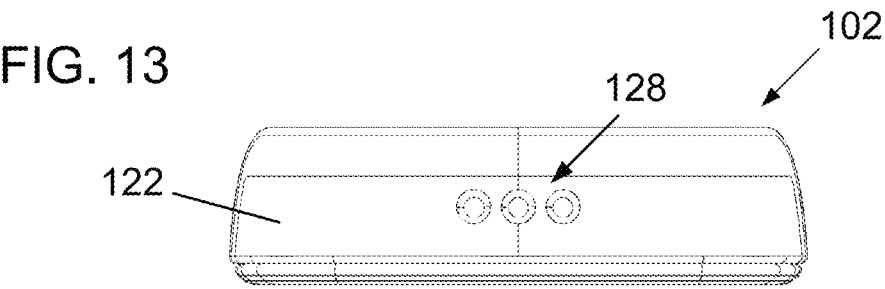
FIG. 13 is an elevational view of a front of the sensor module of FIG. 8.
Figure 14:
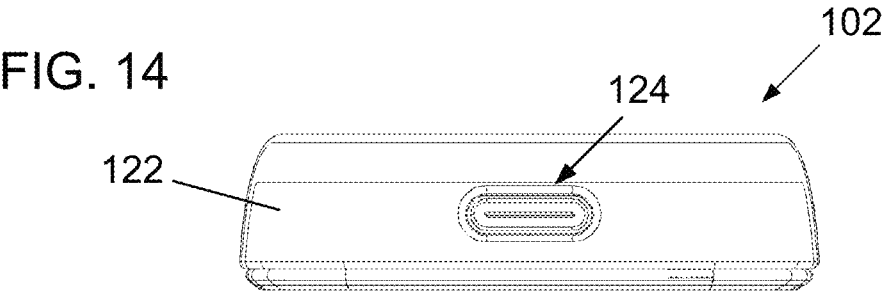
FIG. 14 is an elevational view of a back of the sensor module of FIG. 8.
Figure 11A:
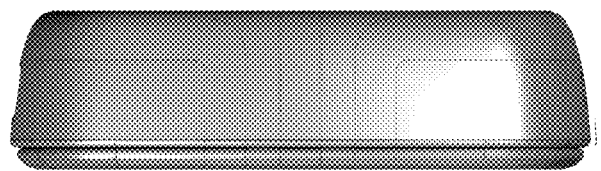
FIG. 11A is a shaded version of the view of FIG. 11.
Figure 12A:
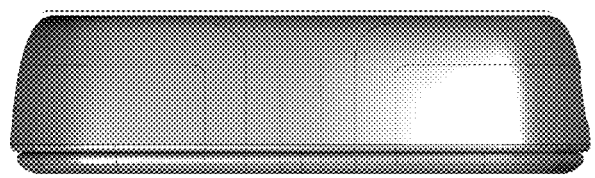
FIG. 12A is a shaded version of the view of FIG. 12.
Figure 13A:
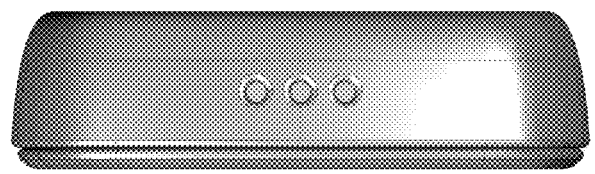
FIG. 13A is a shaded version of the view of FIG. 13.
Figure 14A:
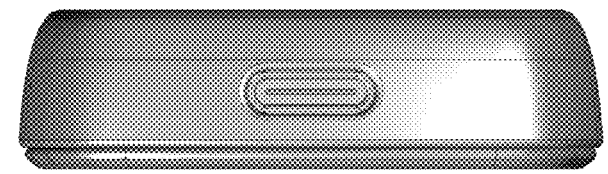
FIG. 14A is a shaded version of the view of FIG. 14.
Figure 15:
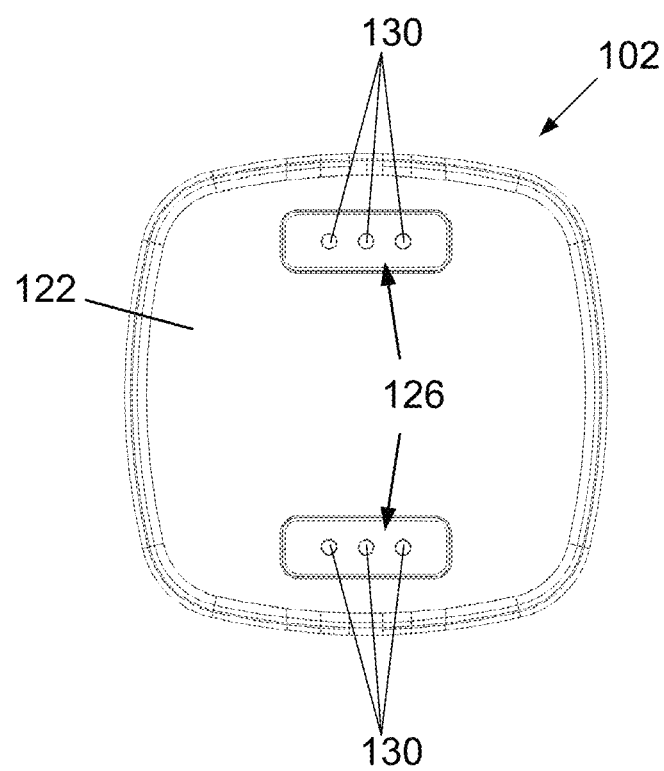
FIG. 15 is a bottom plan view of the sensor module of FIG. 8.
Figure 15A:
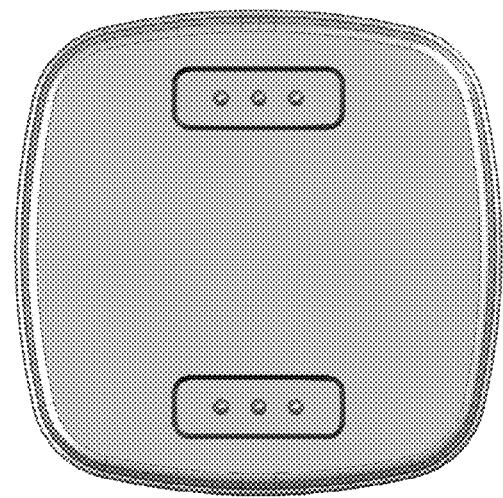
FIG. 15A is a shaded version of the view of FIG. 15.
Figure 16:
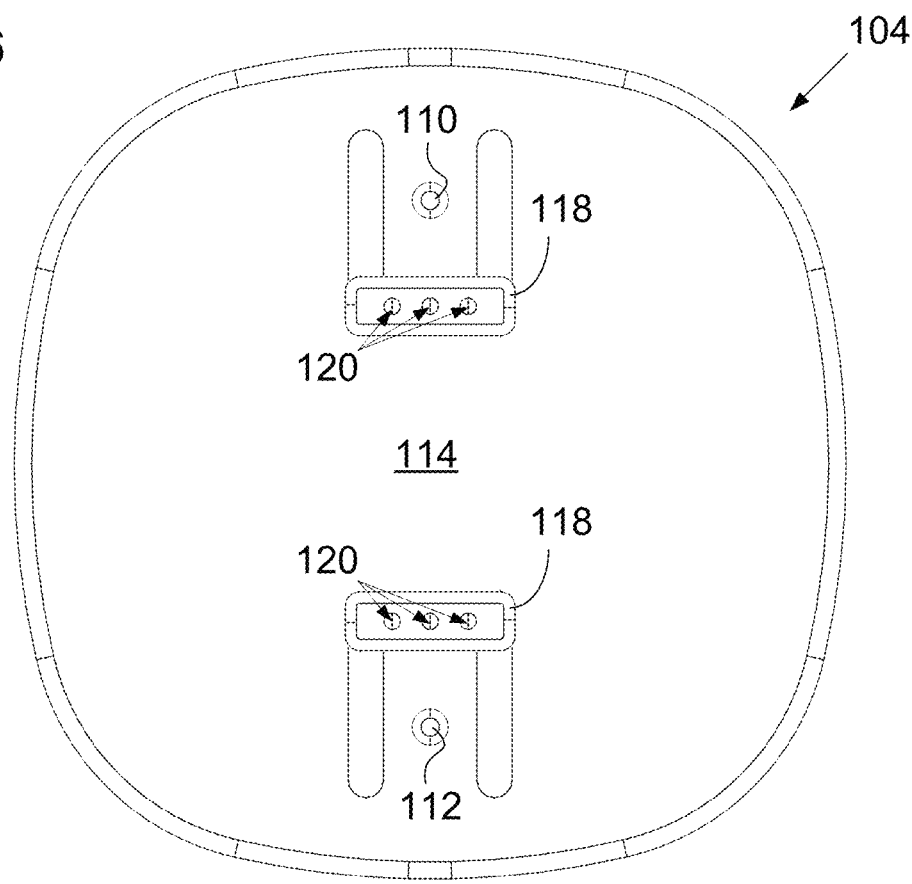
FIG. 16 is a top plan view of a sensor base of the sensor of FIG. 1.
Figure 17:
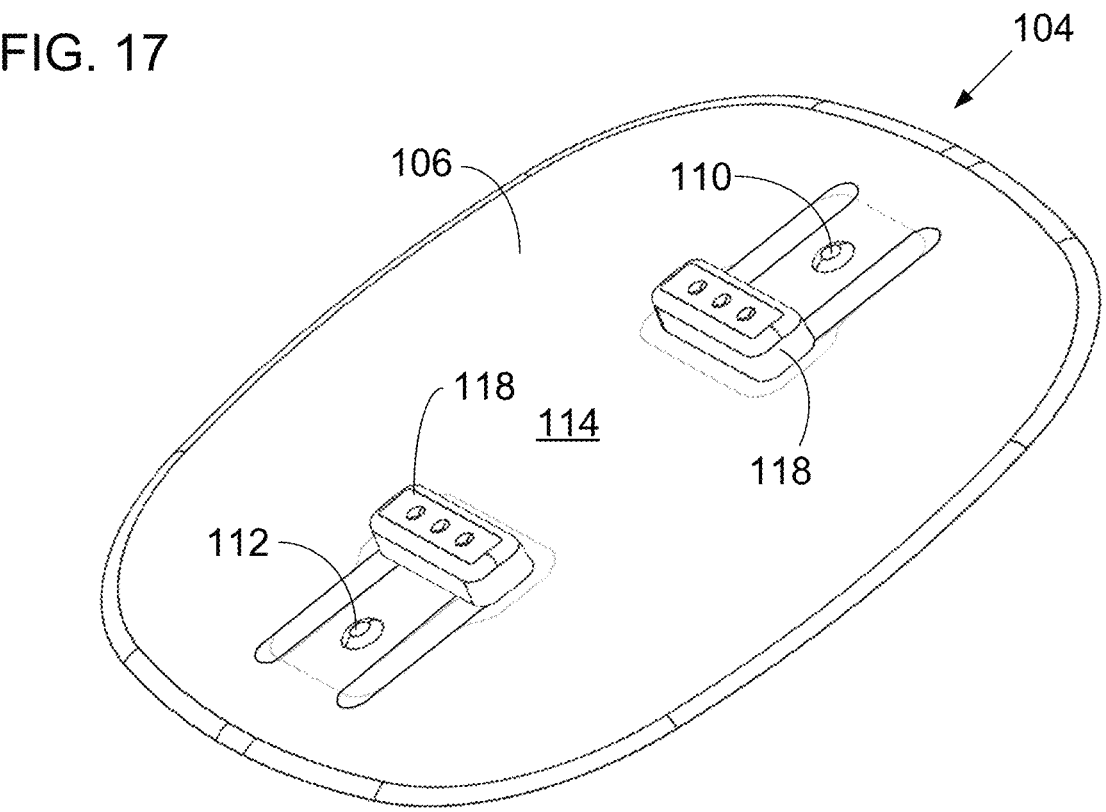
FIG. 17 is a perspective view of the sensor base of FIG. 16.
Figure 16A:
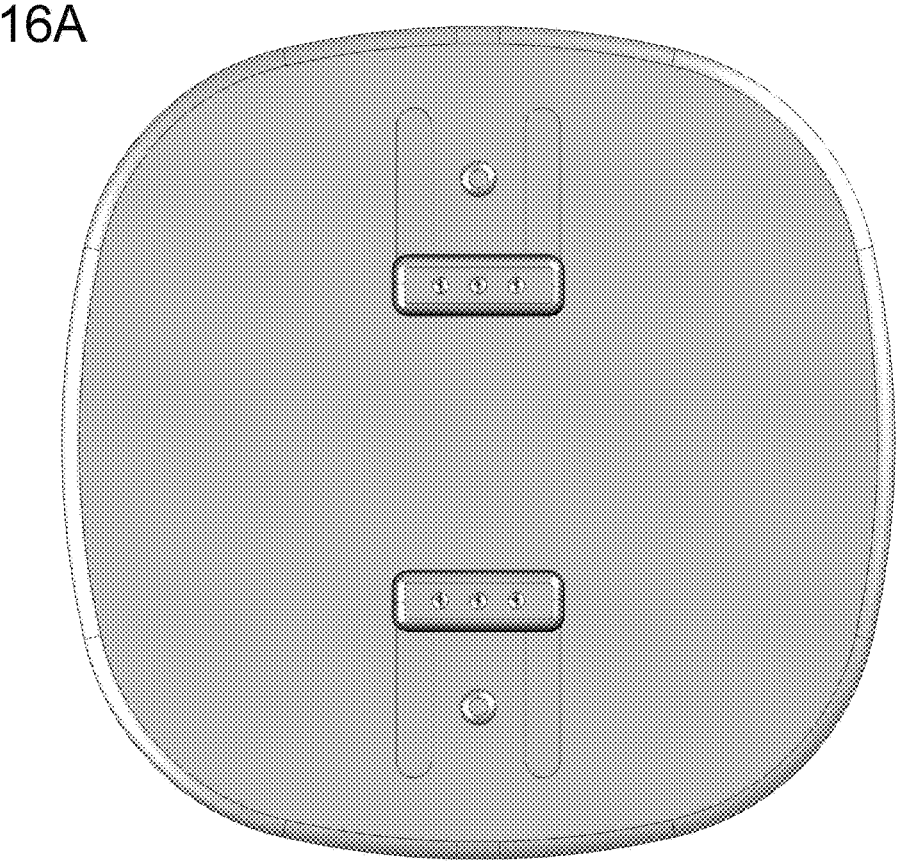
FIG. 16A is a shaded version of the view of FIG. 16.
Figure 17A:
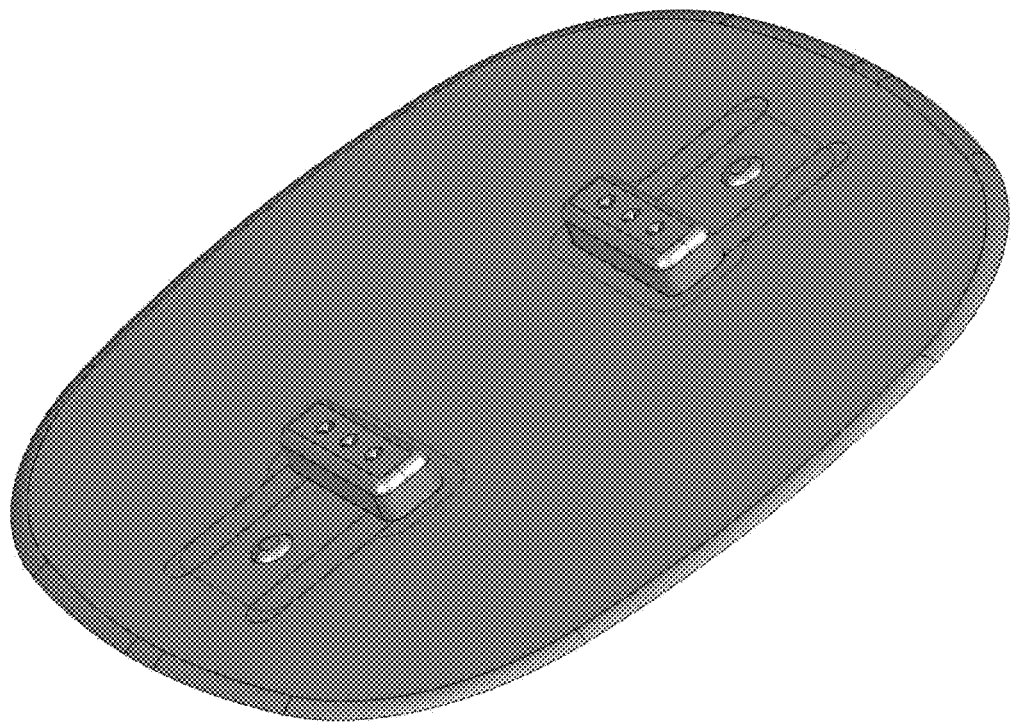
FIG. 17A is a shaded version of the view of FIG. 17.
Figure 18:
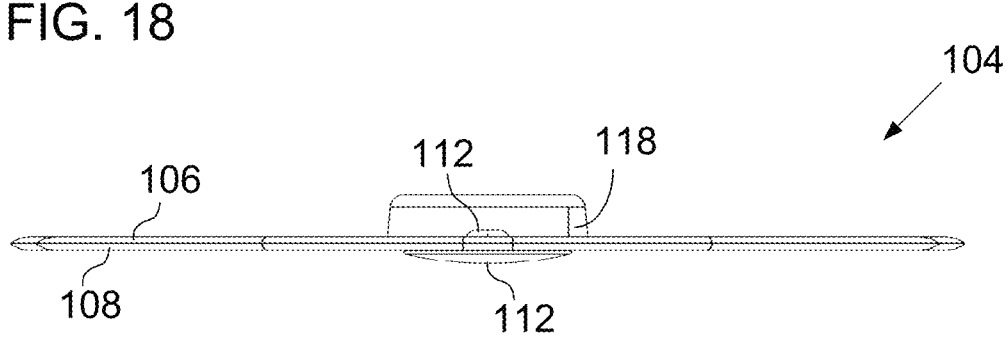
FIG. 18 is an elevational view of a first side of the sensor base of FIG. 16.
Figure 19:
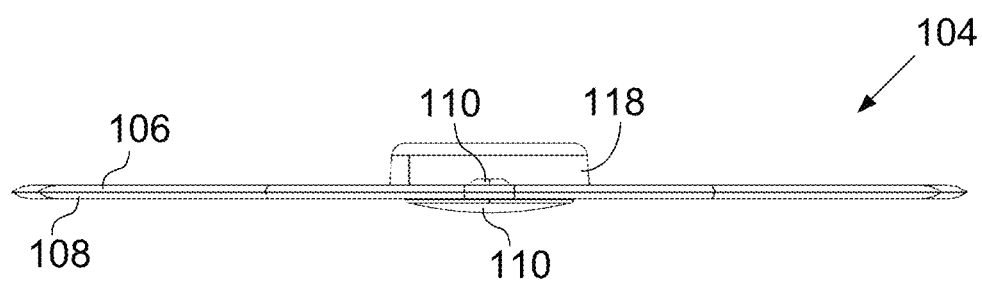
FIG. 19 is an elevational view of a second side of the sensor base of FIG. 16.
Figure 20:
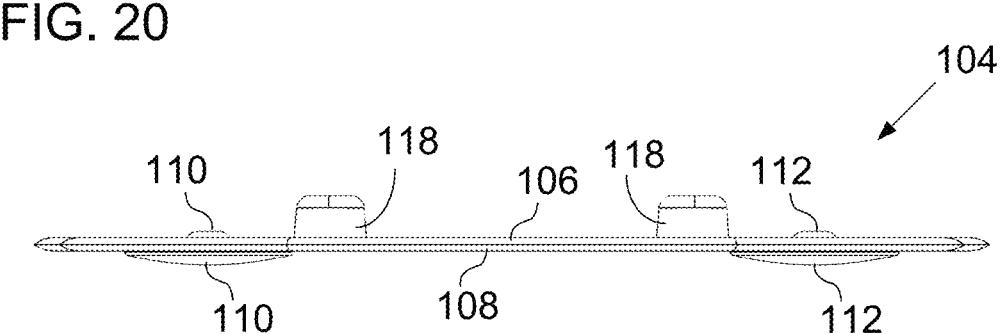
FIG. 20 is an elevational view of a front of the sensor base of FIG. 16.
Figure 21:
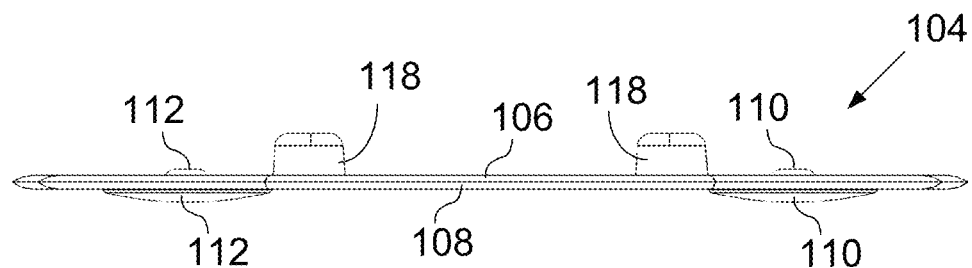
FIG. 21 is an elevational view of a back of the sensor base of FIG. 16.
Figure 18A:
FIG. 18A is a shaded version of the view of FIG. 18.
Figure 19A:
FIG. 19A is a shaded version of the view of FIG. 19.
Figure 20A:
FIG. 20A is a shaded version of the view of FIG. 20.
Figure 21A:
FIG. 21A is a shaded version of the view of FIG. 21.
Figure 22:
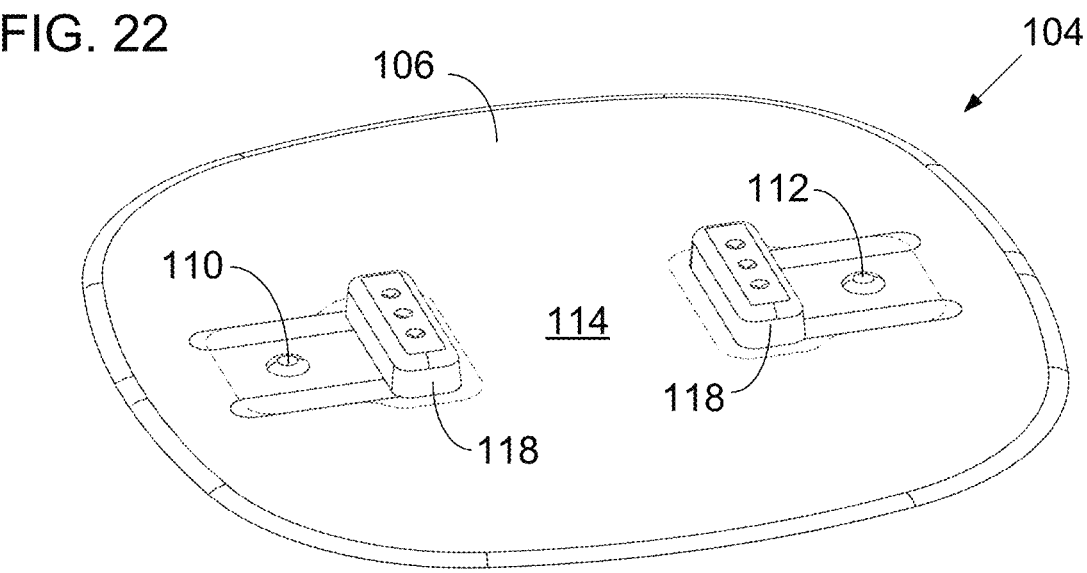
FIG. 22 is another perspective view of the sensor base of FIG. 16.
Figure 23:
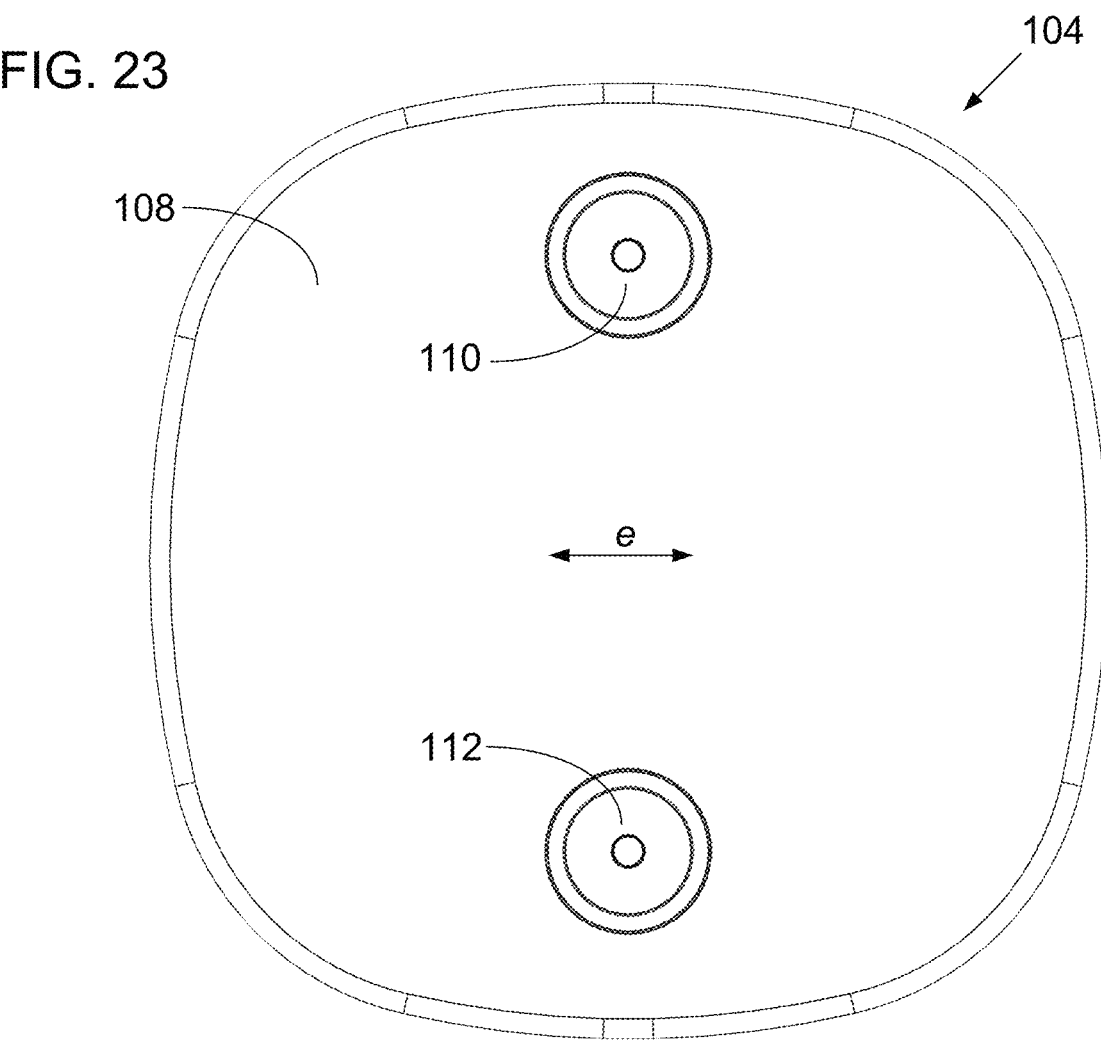
FIG. 23 is a bottom plan view of the sensor base of FIG. 16.
Figure 22A:
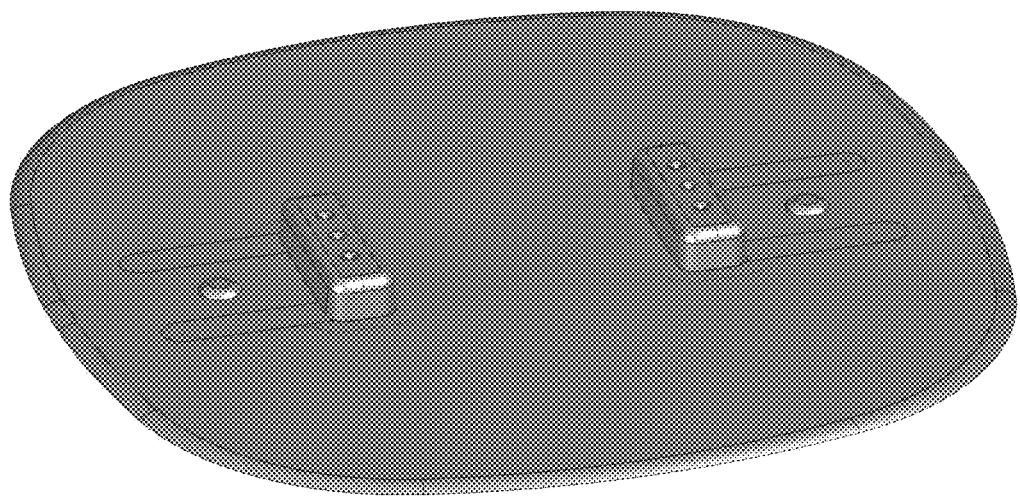
FIG. 22A is a shaded version of the view of FIG. 22.
Figure 23A:
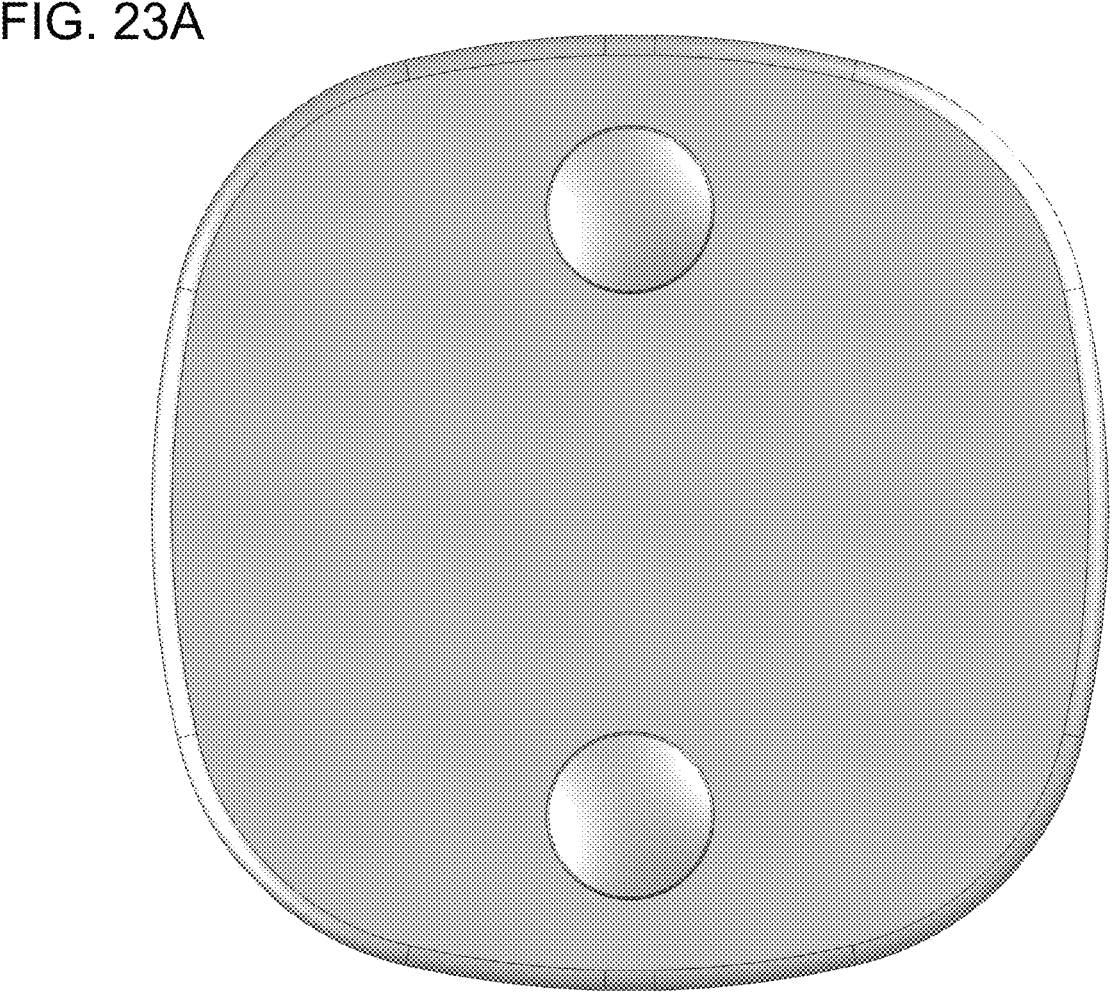
FIG. 23A is a shaded version of the view of FIG. 23.
Figure 25:
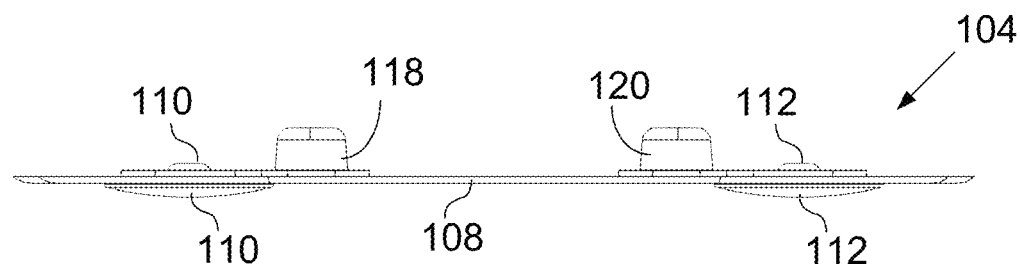
FIG. 25 is the front elevational view of the sensor base as seen in FIG. 20, wherein the top layer is omitted.
Figure 26:
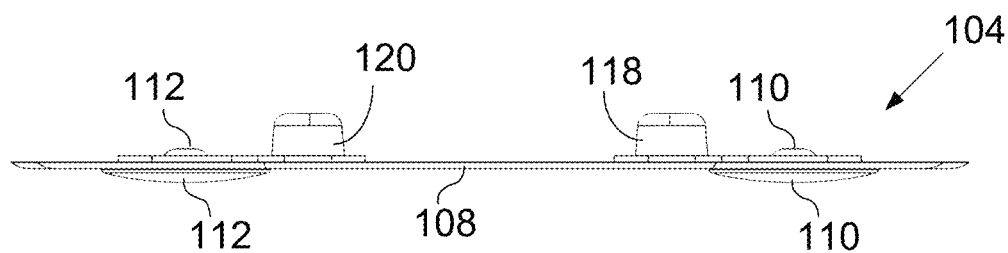
FIG. 26 is the back elevational view of the sensor base as seen in FIG. 21, wherein the top layer is omitted.
Figure 25A:
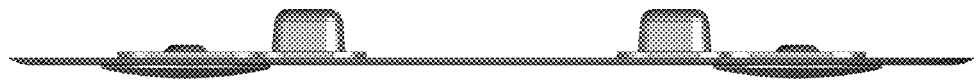
FIG. 25A is a shaded version of the view of FIG. 25.
Figure 26A:
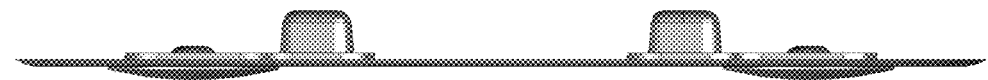
FIG. 26A is a shaded version of the view of FIG. 26.

Turning now to the drawings, it should first be noted that each of FIGS. 1-34 has a corresponding shaded version designated with the same number followed by an "A". The shaded version is presented for additional illustration. In this respect, FIG. 1A is a shaded version of the view of FIG. 1; FIG. 2A is a shaded version of the view of FIG. 2; FIG. 3A is a shaded version of the view of FIG. 3; FIG. 4A is a shaded version of the view of FIG. 4; FIG. 5A is a shaded version of the view of FIG. 5; FIG. 6A is a shaded version of the view of FIG. 6; FIG. 7A is a shaded version of the view of FIG. 7; FIG. 8A is a shaded version of the view of FIG. 8; FIG. 9A is a shaded version of the view of FIG. 9; FIG. 10A is a shaded version of the view of FIG. 10; FIG. 11A is a shaded version of the view of FIG. 11; FIG. 12A is a shaded version of the view of FIG. 12; FIG. 13A is a shaded version of the view of FIG. 13; FIG. 14A is a shaded version of the view of FIG. 14; FIG. 15A is a shaded version of the view of FIG. 15; FIG. 16A is a shaded version of the view of FIG. 16; FIG. 17A is a shaded version of the view of FIG. 17; FIG. 18A is a shaded version of the view of FIG. 18; FIG. 19A is a shaded version of the view of FIG. 19; FIG. 20A is a shaded version of the view of FIG. 20; FIG. 21A is a shaded version of the view of FIG. 21; FIG. 22A is a shaded version of the view of FIG. 22; FIG. 23A is a shaded version of the view of FIG. 23; FIG. 24A is a shaded version of the view of FIG. 24; FIG. 25A is a shaded version of the view of FIG. 25; FIG. 26A is a shaded version of the view of FIG. 26; FIG. 27A is a shaded version of the view of FIG. 27; FIG. 28A is a shaded version of the view of FIG. 28; FIG. 29A is a shaded version of the view of FIG. 29; FIG. 30A is a shaded version of the view of FIG. 30; FIG. 31A is a shaded version of the view of FIG. 31; FIG. 32A is a shaded version of the view of FIG. 32; FIG. 33A is a shaded version of the view of FIG. 33; and FIG. 34A is a shaded version of the view of FIG. 34.

First Sensor Embodiment

Referring now to FIGS. 1-7, a sensor 100 in accordance with one or more aspects and features of the invention is illustrated. The sensor 100 preferably is electro-myographic.

Figure 1A:
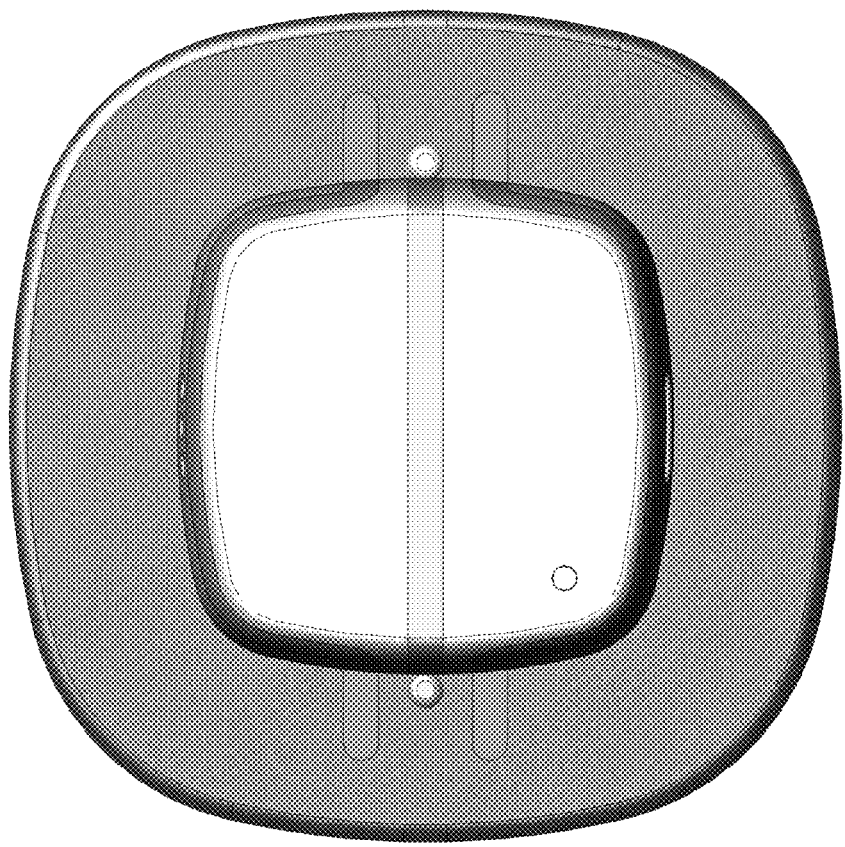
FIG. 1A is a shaded version of the view of FIG. 1.

In particular, FIG. 1 is a top plan view of the sensor 100; FIG. 2 is a perspective view of the sensor 100; and FIG. 3 is an elevational view of a first side of the sensor 100; FIG. 4 is an elevational view of a second side of the sensor 100; FIG. 5 is an elevational view of a front of the sensor 100; FIG. 6 is an elevational view of a back of the sensor 100; and FIG. 7 is a bottom plan view of the sensor 100.

The sensor 100 comprises a sensor module 102. FIG. 8 is a top plan view of the sensor module 102; FIG. 9 is a perspective view of a top of the sensor module 102; FIG. 10 is a perspective view of a bottom of the sensor module 102; FIG. 11 is an elevational view of a first side of the sensor module 102; FIG. 12 is an elevational view of a second side of the sensor module 102; FIG. 13 is an elevational view of a front of the sensor module 102; FIG. 14 is an elevational view of a back of the sensor module 102; and FIG. 15 is a bottom plan view of the sensor module 102.

The sensor 100 further comprises a sensor base 104. FIG. 16 is a top plan view of the sensor base 104; FIG. 17 is a perspective view of the sensor base 104; FIG. 18 is an elevational view of a first side of the sensor base 104; FIG. 19 is an elevational view of a second side of the sensor base 104; FIG. 20 is an elevational view of a front of the sensor base 104; FIG. 21 is an elevational view of a back of the sensor base 104; FIG. 22 is another perspective view of the sensor base 104; and FIG. 23 is a bottom plan view of the sensor base 104.

The sensor base 104 preferably comprises a fabric article and, more preferably, comprises a multi-layer fabric article. As seen in FIGS. 18-21, the sensor base 104 comprises a top layer 106 and a bottom layer 108. The top layer 106 and bottom layer 108 are secured together by electrodes 110,112 of the sensor base 104 that extend on opposite sides of the sensor base 104 proximate the top surface 114 and bottom surface 116 of the sensor base 104. Furthermore, the bottom layer 108 preferable comprises an adhesive surface for adhering the sensor base 104 to a person's skin, together with a peal-away outer sheet for covering the adhesive surface until such use is intended.

The top layer 106 and bottom layer 108 also preferably comprise kinesiology tape, which is believed to have an elasticity along the lengthwise direction with no elasticity in the widthwise direction; however, other tape and other substrates-whether elastic or inelastic—also are contemplated for forming the sensor base 104 in accordance with aspects and features of the invention. Kinesiology tape is preferred because use of such tape is believed to provide the advantages of using such tape in addition to the advantages provided by a sensor in accordance with one or more aspects and features of the invention which sensor does not use kinesiology tape. The layers are cut from the tape so as to have a predefined shape or "footprint". The footprint preferably is die-cut but may be made by stamping, laser cutting, or other methods in lieu of die cutting. The footprint of the sensor base 104 as seen in FIGS. 1-7 and 16-23 is that of a rounded square, with a lengthwise direction of elastic stretching being located along a front-and-back axis as opposed to a side-to-side axis, whereby the distance between the electrodes 110,112 does not varying with stretching of the sensor base 140. An exemplary axis of elasticity e of the sensor base 104 is illustrated in FIG. 23. Additional footprints are contemplated and additional exemplary footprints are disclosed below.

It further will be noted and appreciated that when the top layer 106 is formed from kinesiology tape, the adhesive bottom surface of the top layer 106 attaches to and further secures the top layer 106 to the upper surface of the bottom layer 108. Furthermore, when using kinesiology tape, printed graphics can be included on the top surface of the tape for aesthetic purposes. An example of this is seen below with reference to sensor 1100, wherein "BIO-BACK 7000" is printed on a translucent top layer of the sensor base 1104 such that it appears over an embedded conductive tape 1160 that is sandwiched between the layers of the sensor base 1104.

Figure 24:
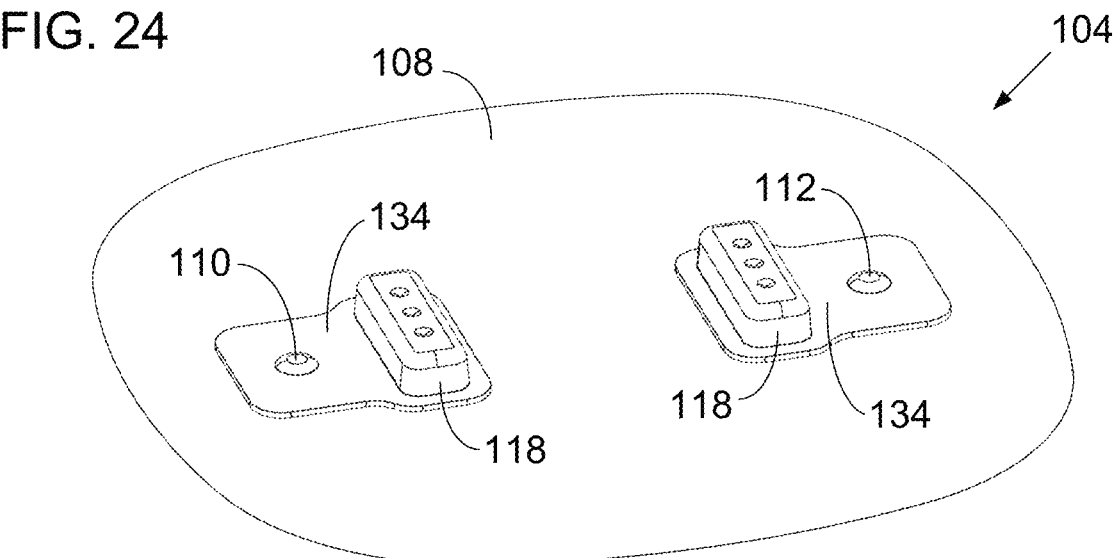
FIG. 24 is a perspective view of the sensor base seen in FIG. 24, wherein a top layer is omitted.
Figure 24A:
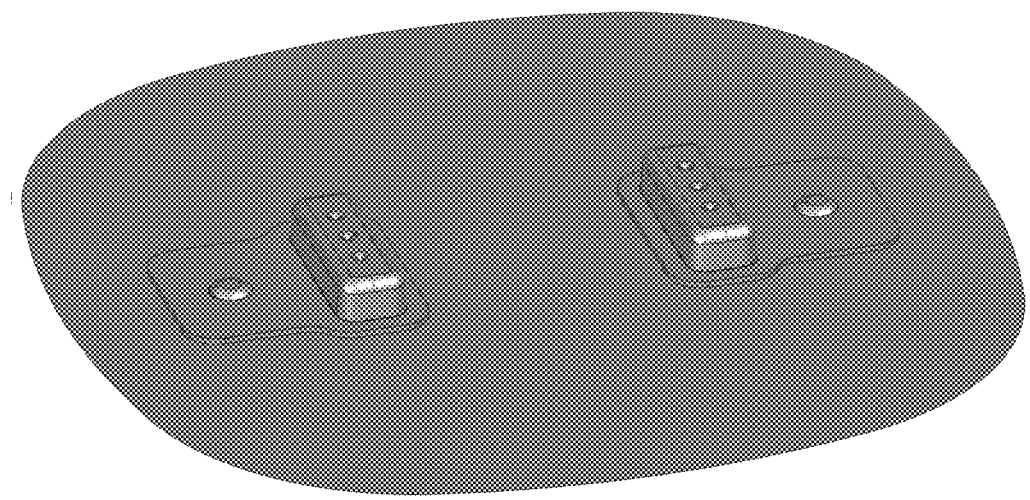
FIG. 24A is a shaded version of the view of FIG. 24.

FIG. 24 is another perspective view of the sensor base 104, wherein the top layer 106 of the base 104 is omitted; FIG. 25 is the front elevational view of the sensor base 104 as seen in FIG. 20, wherein the top layer 106 also is omitted; and FIG. 26 is the back elevational view of the sensor base 104 as seen in FIG. 21, wherein the top layer 106 also is omitted.

The sensor module 102 comprises a casing 122 containing circuitry preferably in the form of a circuit board for sensor operations (not shown in FIGS. 1-15; shown as component 950 in FIG. 49 with respect to sensor 900); a microcontroller; a transceiver for wireless communications (not shown); a rechargeable battery for powering the sensor (not shown), the recharging of which is accomplish through connection of charging port 124 with a power source preferably using a USB cable; an attachment structure preferably in the form of recesses 126 formed in the casing 122 for releasable engagement of the sensor module 102 and the sensor 104; and an interface preferably in the form of electrical pins 130 (see FIG. 10) extending downwardly within the recesses 126 for electrically connecting the circuit board to electrodes 110,112 of the sensor base 104.

The wireless communications preferably are Bluetooth™ communications, but may comprise additionally or alternatively Wi-Fi™ communications and ZigBee™ communications.

The casing 122 of the sensor module 102 also preferably contains a component for alerting a person wearing the sensor, which preferably comprises a vibration mechanism (not shown) or a speaker for auditory alerts (not shown, but for which audio openings 128 are provided in a side wall of the casing 122).

The sensor module 102 further preferably comprises a light emitting component, such as an LED 132, for indicating a level of electric charge of the rechargeable battery.

The sensor base 104 comprises an attachment structure preferably in the form of protuberances 118 that correspond to the recesses 126 for frictional fit therein for releasable engagement of the sensor module 102 and the sensor base 104; an interface preferably in the form of pin openings 120 for receiving the electrical pins 130 of the sensor module 102 for electrical connection and communication between the electrodes 110,112 of the sensor base 104 and the circuitry of the sensor module 102; and electrical pathways (not shown) connecting the electrodes 110,112 and to the electrical pins 130 when received within the pin openings 120. Furthermore, the electrodes 110,112 preferably are in the form of dry surface electromyography (EMG) electrodes. Use of gel electrodes also is preferred in aspects and features of the invention. A bracket 134 preferably comprising stamped sheet metal connects the protuberance 118 to a respective electrode 110,112 as perhaps best seen in FIG. 24, which bracket is sandwiched between the top layer 106 and the bottom layer 108.

In operation, when the sensor module 102 is releasably engaged with the sensor base 104, and the sensor base 104 is attached to a person's skin proximate a targeted muscle or muscle group, the sensor 100 measures electrical activity of the muscle or muscle group, which varies during contraction and relaxation. Based on a predetermined profile, the measured electrical activity is used to determine transitions from relaxation to contraction of the muscle or muscle group, and a degree of contraction, and transitions from contraction to relaxation of the muscle or muscle group. The predetermined profile can be preset within a nontransitory memory of the circuitry of the sensor 100 and can be determined from past measurements taken to establish such transitions and degrees of contraction. Moreover, a large set of data preferably is acquired and machine learning applied for determining the predetermined profile. The predetermined profile furthermore preferably is determined for each particular individual during setup of the sensor; however, it is contemplated that a standardized profile may be established for use with a plurality of persons.

Additional Exemplary Footprints

Figure 27:
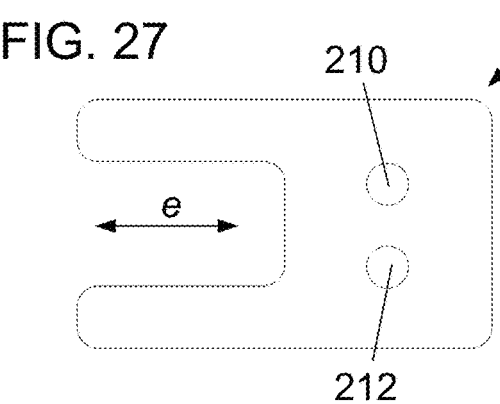
FIG. 27 is a bottom plan view of another sensor base in accordance with one or more aspects and features of the invention.
Figure 28:
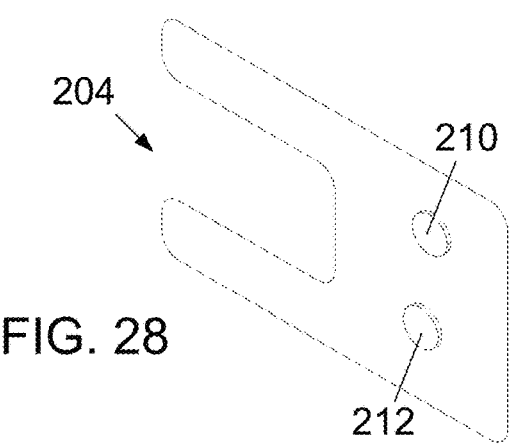
FIG. 28 is a perspective view of the sensor base of FIG. 27.
Figure 27A:
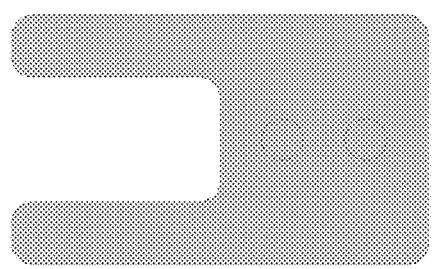
FIG. 27A is a shaded version of the view of FIG. 27.
Figure 28A:
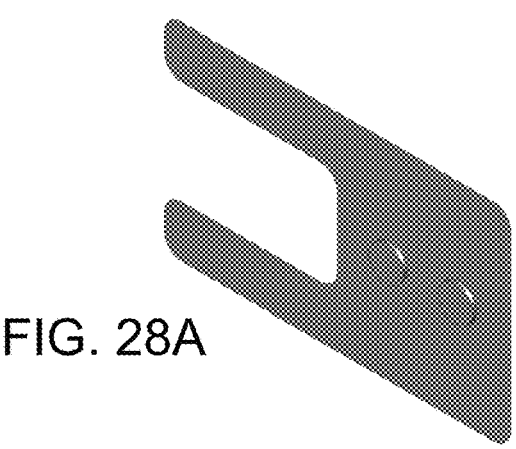
FIG. 28A is a shaded version of the view of FIG. 28.

FIG. 27 is a bottom plan view of another sensor base 204 in accordance with one or more aspects and features of the invention; and FIG. 28 is a perspective view of the sensor base 204. Sensor base 204 is similar to sensor base 104 and includes electrodes 210,212; however, unlike sensor base 104, sensor base 204 has a different shape or footprint that includes a "U" shaped portion. Such tape preferably has a bilinear elasticity along the lengthwise direction with no elasticity in the widthwise direction.

Figure 29:
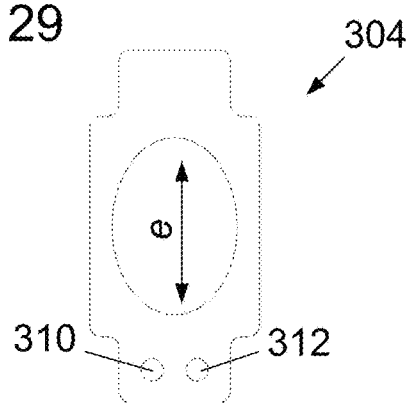
FIG. 29 is a bottom plan view of another sensor base in accordance with one or more aspects and features of the invention.
Figure 30:
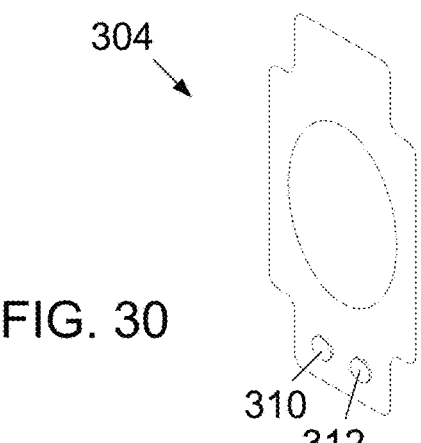
FIG. 30 is a perspective view of the sensor base of FIG. 29.
Figure 29A:
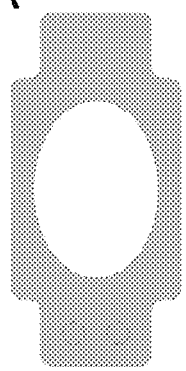
FIG. 29A is a shaded version of the view of FIG. 29.
Figure 30A:
FIG. 30A is a shaded version of the view of FIG. 30.

FIG. 29 is a bottom plan view of another sensor base 304 in accordance with one or more aspects and features of the invention; and FIG. 30 is a perspective view of the sensor base 304. Sensor base 304 is similar to sensor base 104 and includes electrodes 310,312; however, unlike sensor base 104, sensor base 304 has a different shape or footprint that includes a bounded opening for an elbow. Such footprint preferably has a bilinear elasticity along the lengthwise direction with no elasticity in the widthwise direction.

Figure 31:
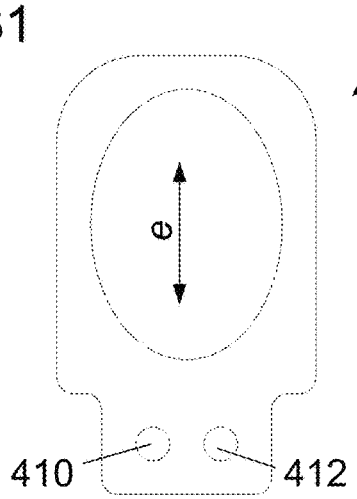
FIG. 31 is a bottom plan view of another sensor base in accordance with one or more aspects and features of the invention.
Figure 32:
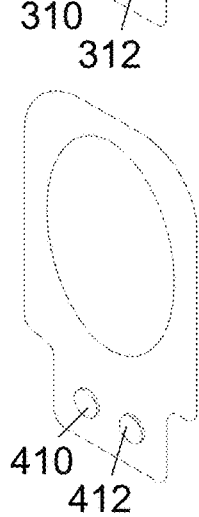
FIG. 32 is a perspective view of the sensor base of FIG. 31.
Figure 31A:
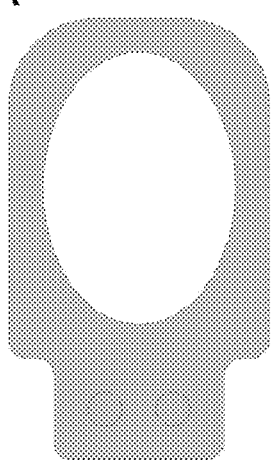
FIG. 31A is a shaded version of the view of FIG. 31.
Figure 32A:
FIG. 32A is a shaded version of the view of FIG. 32.

FIG. 31 is a bottom plan view of another sensor base 404 in accordance with one or more aspects and features of the invention; and FIG. 32 is a perspective view of the sensor base 404. Sensor base 404 is similar to sensor base 104 and includes electrodes 410,412; however, unlike sensor base 104, sensor base 404 has a different shape or footprint that includes a bounded opening for a knee. Such footprint preferably has a bilinear elasticity along the lengthwise direction with no elasticity in the widthwise direction.

Figure 33:
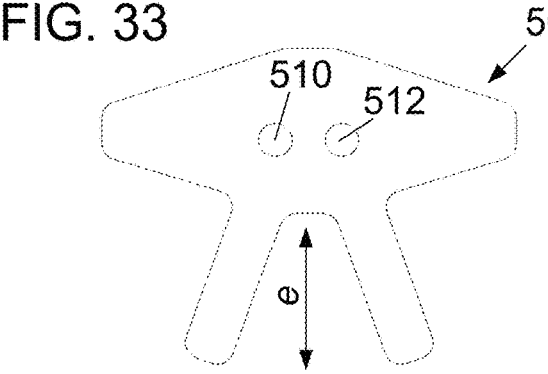
FIG. 33 is a bottom plan view of another sensor base in accordance with one or more aspects and features of the invention.
Figure 34:
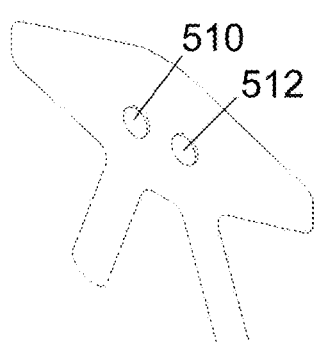
FIG. 34 is a perspective view of the sensor base of FIG. 33.
Figure 33A:
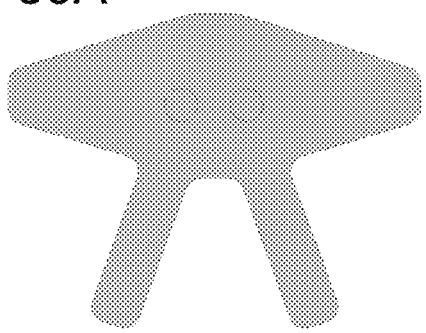
FIG. 33A is a shaded version of the view of FIG. 33.
Figure 34A:
FIG. 34A is a shaded version of the view of FIG. 34.

FIG. 33 is a bottom plan view of another sensor 504 base in accordance with one or more aspects and features of the invention; and FIG. 34 is a perspective view of the sensor base 504. Sensor base 504 is similar to sensor base 104 and includes electrodes 510,512; however, unlike sensor base 104, sensor base 504 has a different shape or footprint that includes diverging arms extending away from electrodes 510,512. Such footprint preferably has a bilinear elasticity along the lengthwise direction with no elasticity in the widthwise direction.

Still other footprints are contemplated. For example, a footprint of other sensors each preferably corresponds with a kinesiology taping pattern for a particular muscle or muscle group that is to be monitored using the sensor. Thus, for example, FIG. 35 is a schematic view of a bottom of another sensor base 604 for use proximate a knee in accordance with one or more aspects and features of the invention. The footprint of the sensor base 604 generally corresponds with a kinesiology taping pattern for the knee as seen in FIG. 36.

FIG. 37 is a schematic view of a bottom of another sensor base 704 for use proximate a shoulder in accordance with one or more aspects and features of the invention. The footprint of the sensor base 704 generally corresponds with a kinesiology taping pattern for the shoulder as seen in FIG. 38.

FIG. 39 is a schematic view of a bottom of another sensor base 804 for use proximate an arm in accordance with one or more aspects and features of the invention. The footprint of the sensor base 804 generally corresponds with a kinesiology taping pattern for the arm as seen in FIG. 40. A kinesiology taping pattern for the forearm is seen in FIG. 41, and another footprint for a sensor base generally corresponds with this kinesiology taping pattern, too.

Commercial Version of the Sensor Module

Figure 44:
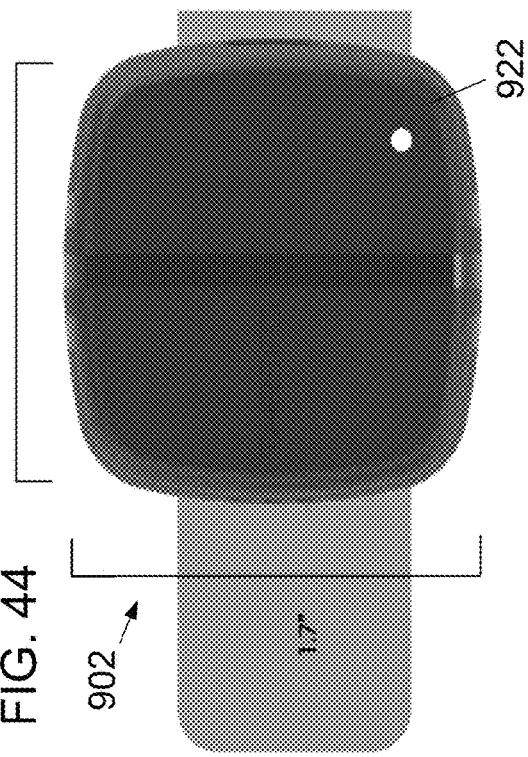
FIG. 44 is a top perspective view of the sensor module of FIG. 42.
Figure 45:
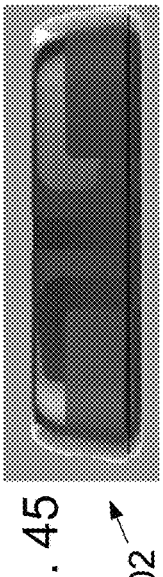
FIG. 45 is a side elevational view of the sensor module of FIG. 42.
Figure 42:
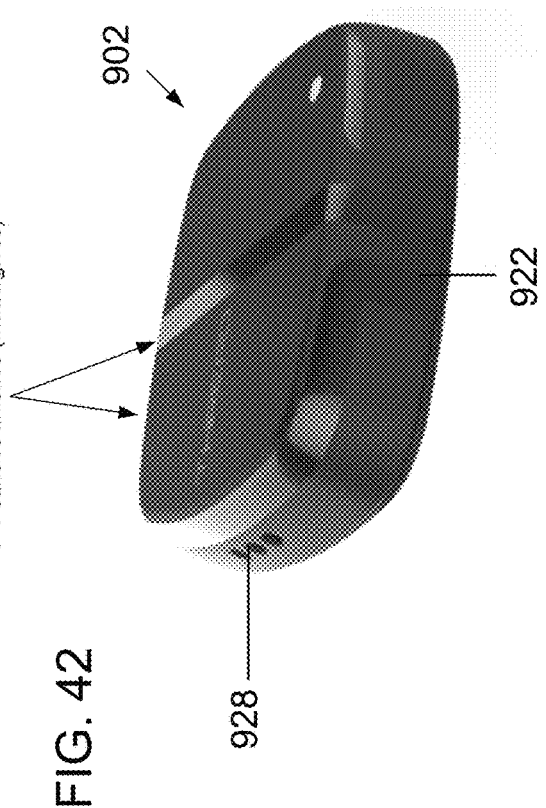
FIG. 42 is a perspective view of a commercial version of the sensor module of FIG. 1 in accordance with one or more aspects and features of the invention.
Figure 43:
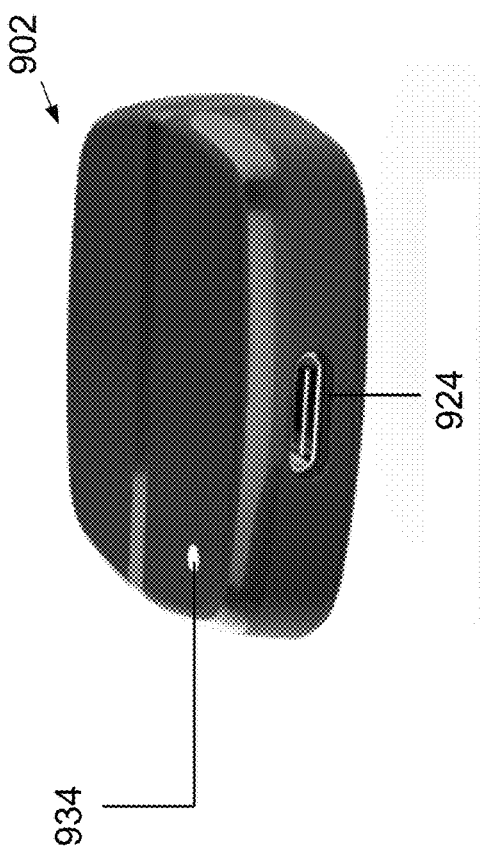
FIG. 43 is another perspective view of the sensor module of FIG. 42.

FIG. 42 is a perspective view of a possible commercial version of a sensor module 902 in accordance with one or more aspects and features of the invention. FIG. 43 is another perspective view of the sensor module 902; FIG. 44 is a top perspective view of the sensor module 902; and FIG. 45 is a side elevational view of the sensor module of FIG. 42. The casing 922 of the sensor module 904 preferably is injection molded, i.e., formed by injection-molding, and includes textured breaks to create a two-surface finish, including a matte finish and a glossy finish. In particular, the casing 922 preferably comprises a two-piece injection-molded polycarbonate body, with a bottom and a top that snap-fit together to form the casing 922. The casing includes audio openings 928 formed in a side wall of the casing 922, and a USB port 924 for recharging of the battery of the sensor module 902. The sensor module 902 further comprises a light emitting component, such as an LED 932, for indicating a level of electric charge of the rechargeable battery.

Figure 47:
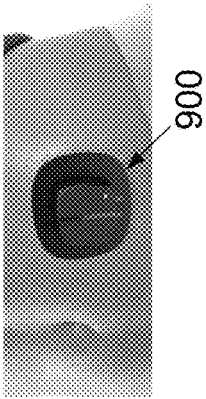
FIG. 47 is an illustration of a sensor—including the sensor module of FIG. 42—being worn by a person for sensing core muscles.
Figure 46:
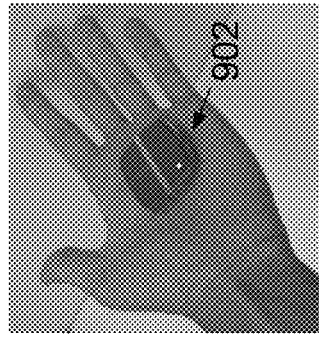
FIG. 46 is an illustration of the sensor module being held in a person's hand.
Figure 48:
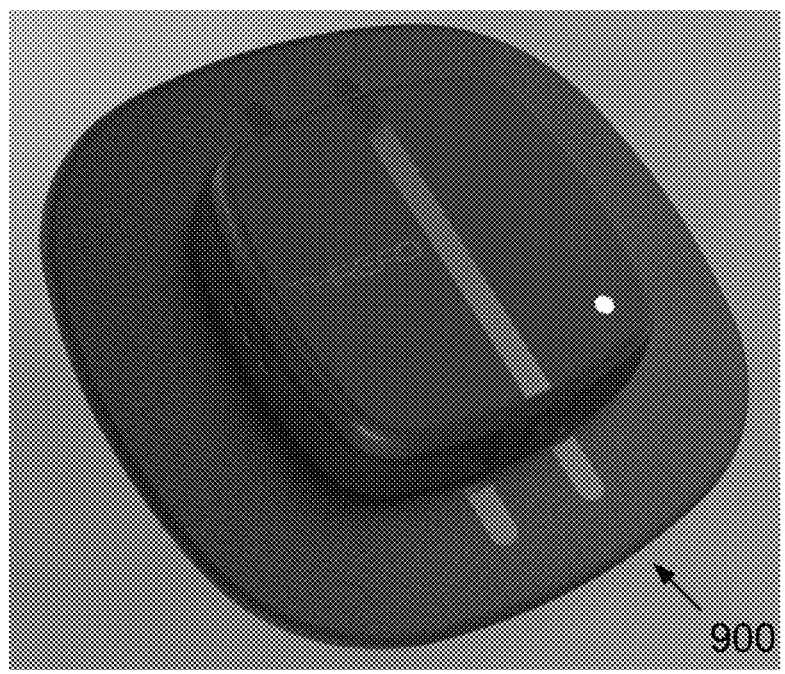
FIG. 48 is a perspective view of the sensor of FIG. 47.

The casing 922 preferable is 1.7 inches in length and 1.7 inches in width, as illustrated in FIG. 44. To give a perspective of size, FIG. 46 illustrates the sensor module 902 being held in a person's hand, and FIG. 47 illustrates a sensor 900—including the sensor module 902—being worn by a person for sensing core muscles; the sensor 900 is seen by itself in a perspective view in FIG. 48.

Figure 49:
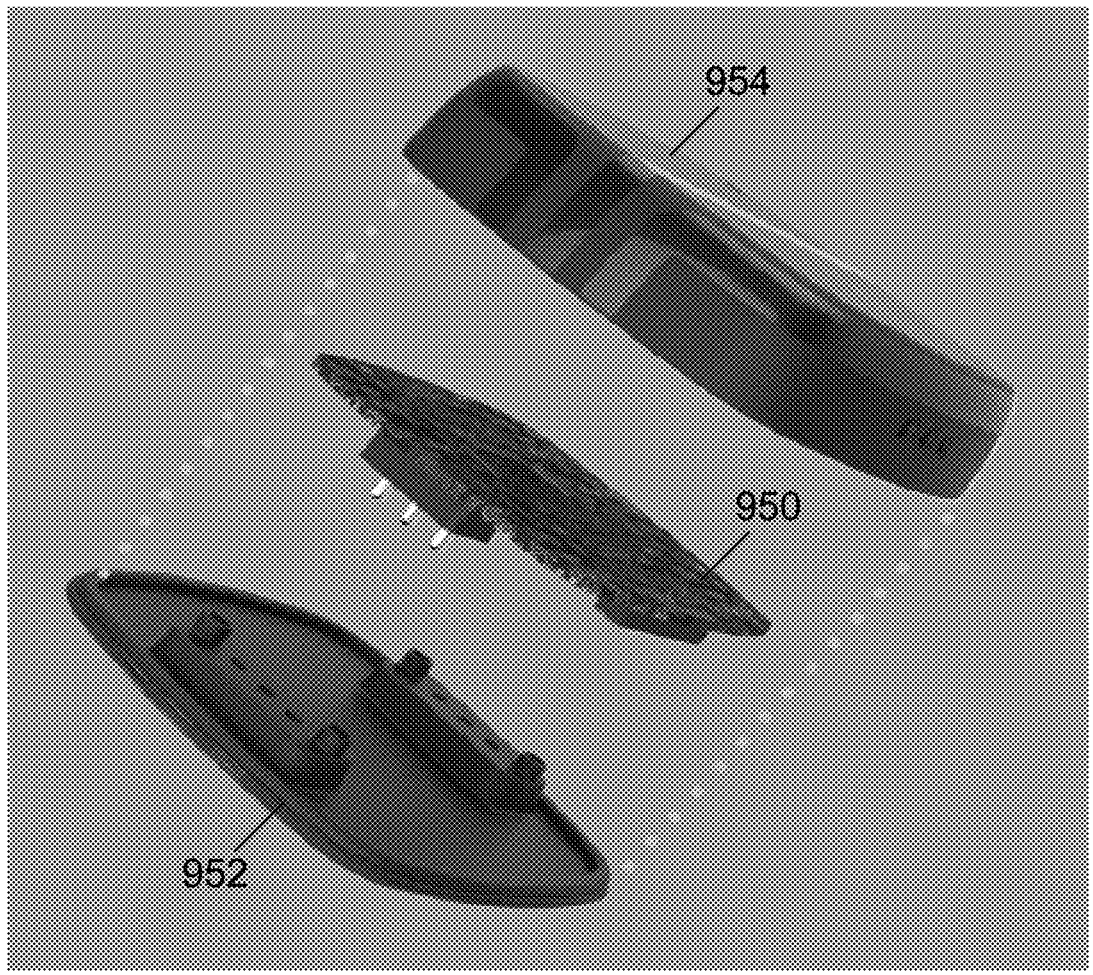
FIG. 49 is a partial exploded view of the sensor module of FIG. 42.

FIG. 49 is a partial exploded view of the casing 922 which illustrates a preferred circuit board contained therein. As seen in FIG. 49, the bottom piece 952 and top piece 954 fit together to form the casing 922 with the circuit board 950 contained therein.

Figure 50:
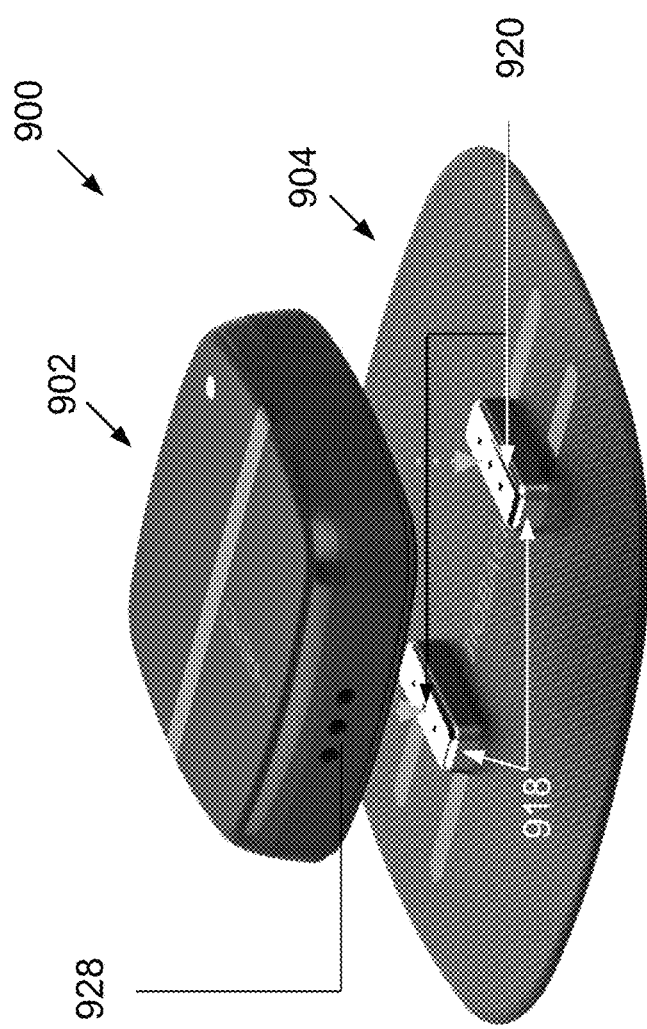
FIG. 50 is a partial exploded view of the sensor of FIG. 47.

FIG. 50 is a partial exploded view of the sensor 900 and serves to illustrate the attachment to and detachment from the sensor base 904 by the sensor module 902. The speaker of the sensor module 902 preferably outputs a confirmation beep when the sensor module 902 is properly attached to the sensor base 904. This is determined when the electrical communication is established by insertion of the pins 930 of the sensor module 902 within the pin openings 920 of the sensor base 904.

Figure 51:
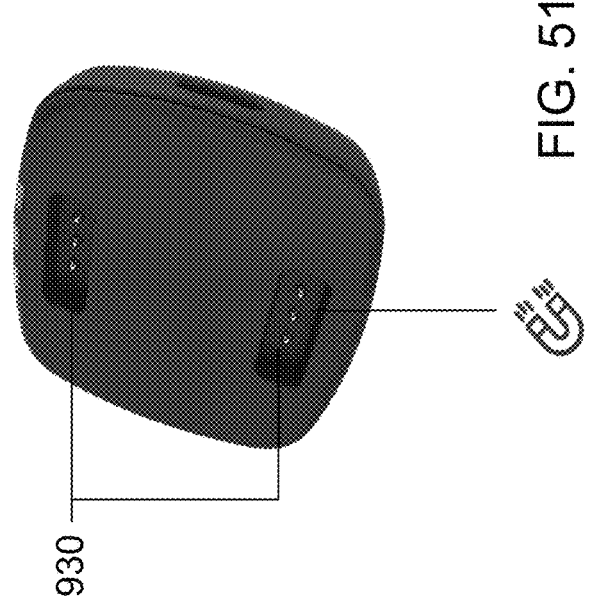
FIG. 51 is a perspective view of the bottom of the sensor module of FIG. 42.

As further illustrated in FIG. 51, which is a perspective view of the bottom of the sensor module 902, magnets may be contained within the sensor module 902 proximate the recesses formed in the casing 922 which magnets attract protuberances 918 of the sensor base 904 for securing the attachment of the sensor module 902 on the sensor base 904, which protuberances 918 may be formed in part from iron, cobalt or nickel.

Figure 52:
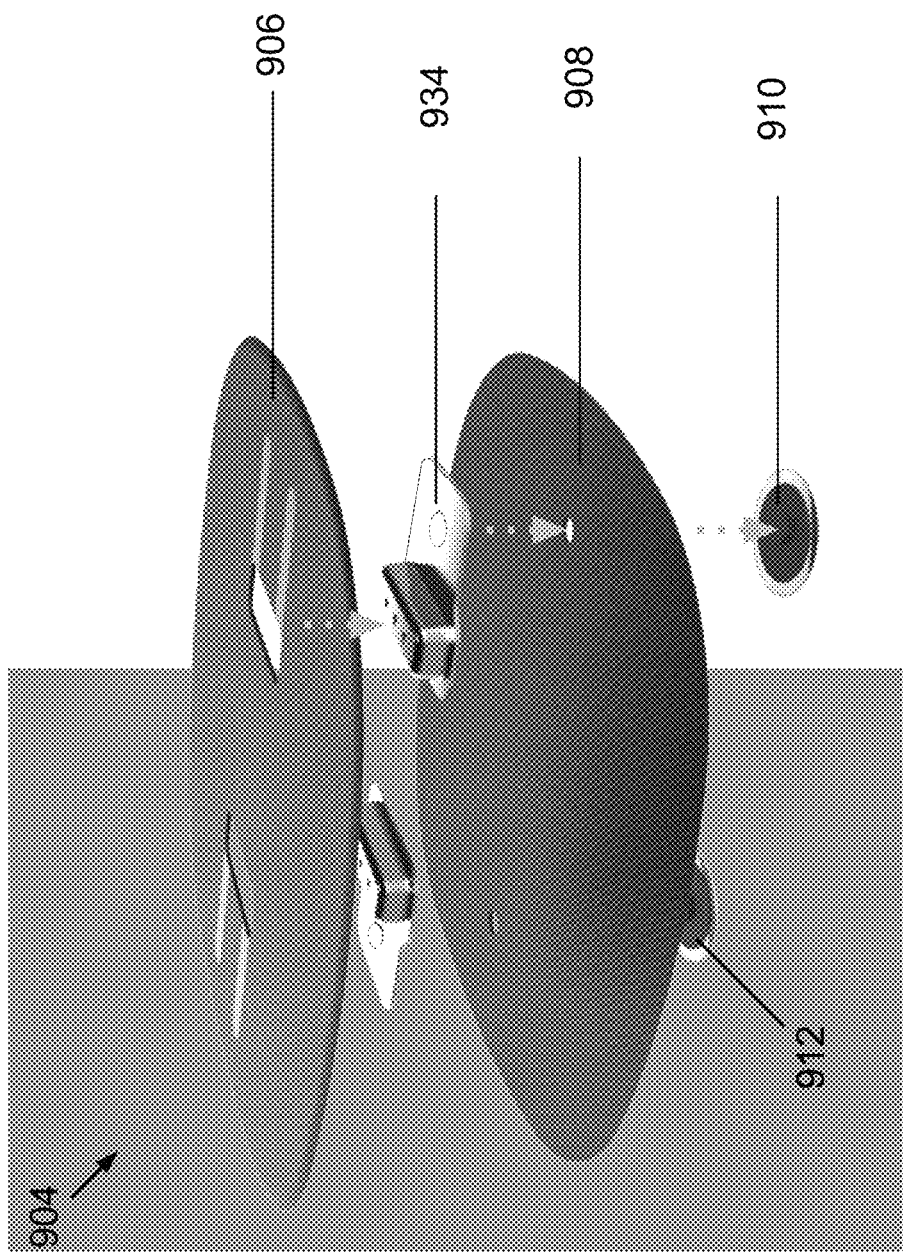
FIG. 52 is a partial exploded view of the sensor base of the sensor of FIG. 47.

FIG. 52 is a partial exploded view of the sensor base 904 of the sensor 900. The exploded view perhaps better shows the sandwiching of the protuberances 918 and brackets 934 between the top layer 906 and the bottom layer 908 of the sensor base 904. Additionally, in this version of the sensor, the electrodes 910,912 do not extend through the top layer 904 and, instead, a portion of the electrodes are crimped to respective brackets 934 between the top layer 904 and the top surfaces of the brackets 934. The electrodes 910,912 also preferably are gel electrodes.

Figure 55:
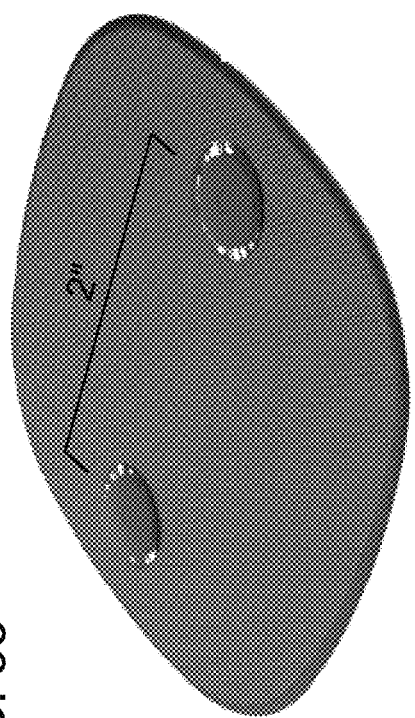
FIG. 55 is a perspective view of the bottom of the sensor base of FIG. 47.
Figure 53:
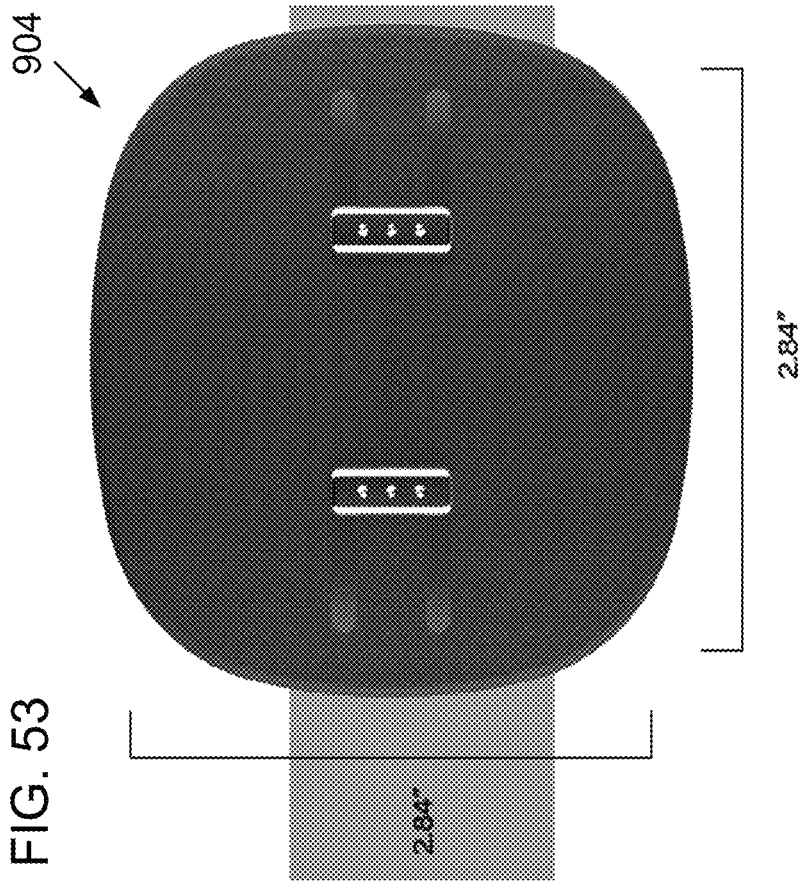
FIG. 53 is a top plan view of the sensor base of FIG. 47.
Figure 54:
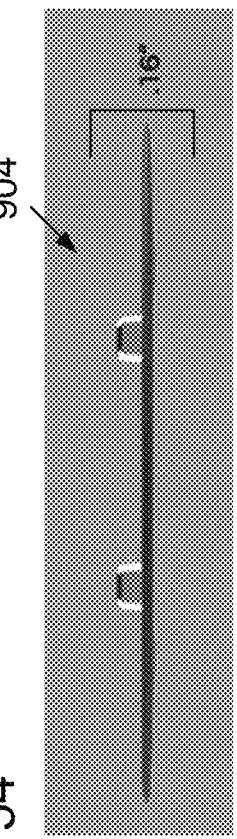
FIG. 54 is a front elevational view of the sensor base of FIG. 47.

FIG. 53 is a top plan view of the sensor base 904, and FIG. 54 is a front elevational view of the sensor base 904. As seen in FIG. 53, the length and width of the sensor base 904 preferably is 2.84 inches and, as seen in FIG. 54, the height of the sensor base 904 is preferably 0.16 inches. As seen in FIG. 55, which is a perspective view of the bottom of the sensor base 904, the electrodes preferably are spaced about 2 inches apart.

Figure 56:
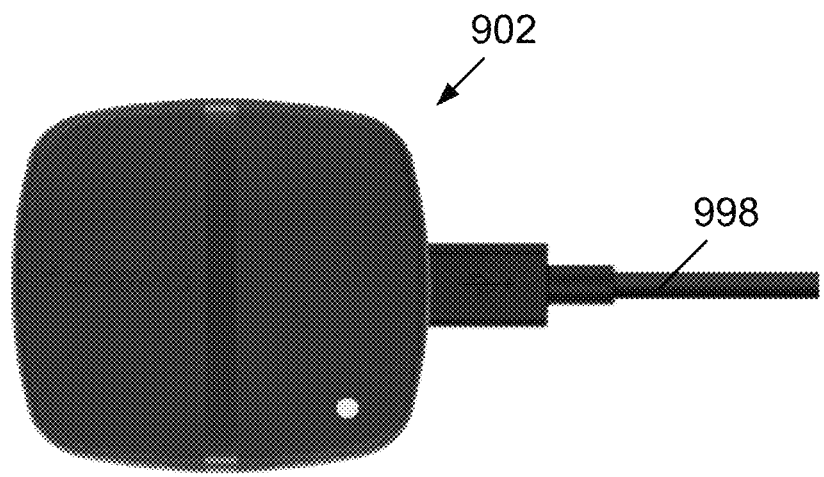
FIG. 56 is a top view of the sensor module of FIG. 42 being charged when the charge is above 80%.
Figure 57:
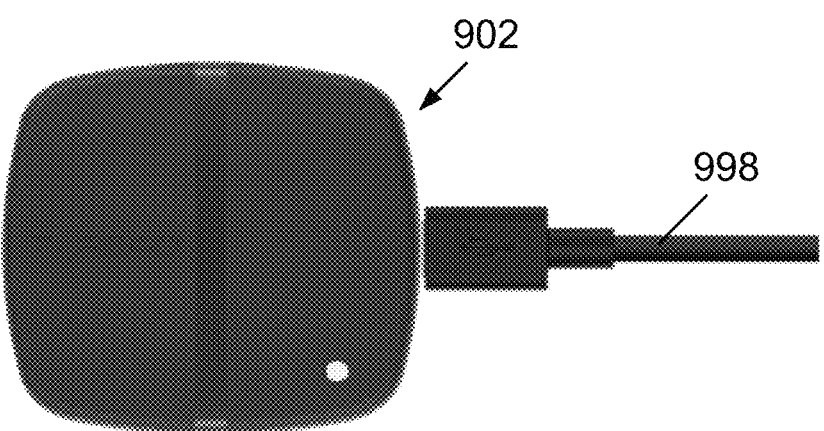
FIG. 57 is a top view of the sensor module of FIG. 42 being charged when the charge is between 20% and 80%.
Figure 58:
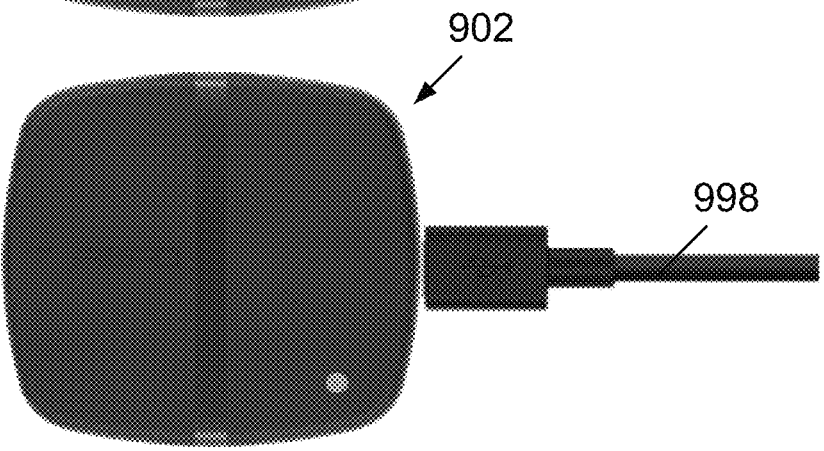
FIG. 58 is a top view of the sensor module of FIG. 42 being charged when the charge is below 20%.

FIGS. 56-58, each of which is a top view of the sensor module 902 seen during charging with a USB cord 998, illustrate that the LED 932 is capable of illuminating different colors for indicating different levels of charge. Preferably, the LED 932 illuminates green when the charge is above 80% (FIG. 56); the LED 932 illuminates yellow when the charge is between 80% and 20% (FIG. 57); and the LED 932 illuminates red when the charge is below 20% (FIG. 58). The LED 932 also could be configured to blink to indicate further information about the sensor module 902. For example, a blinking LED 932 regardless of color could indicate that charging is occurring.

Broad Application and Use of Sensors

It is believed that sensors in accordance with one or more aspects and features of the invention have broad application and use. A preferred application and use is in preventing and treating lower back pain.

In this respect, a sensor in accordance with one or more aspects and features of the invention is attached to the abdomen or back for monitoring core muscles. Based on the monitoring, the sensor detects whether the posture of the person is incorrect and thus may be causing or may lead to lower back pain. When an incorrect posture is detected, the sensor alerts the person through vibration or auditory alert. The alert preferably is given in real time and may be continuous, lasting for the duration of detection of an incorrect posture, or may be intermittent during such detection. Such real time alerting provides immediate feedback to the person regarding the person's posture, enabling the person to adopt and maintain a correct posture without the person unconsciously transitioning to an incorrect posture. It is believed that such biofeedback for posture improvement (i.e., training better back health)—and the consequent posture improvement—will help alleviate lower back pain or prevent lower back pain before it is experienced by a person. Such prevention of injuries while on the job would be particularly beneficial in the workplace or other commercial or industrial setting, whether sitting or standing.

Another exemplary application and use of sensors in accordance with one or more aspects and features of the invention is in sports monitoring and training, including running and strength training. It is believed that monitoring electrical activity of targeted muscles during predefined athletic activities can be used to improve athletic performance. It is believed that this may be particularly true during a sequence of movements of different muscle groups, which occurs, for example, when throwing a football, swinging a bat, or hitting a golf ball. By monitoring and recording the electrical activity of each targeted muscle group with a sensor, and recording the chronological sequence of such activity between the targeted muscle groups, the overall chronological activity of all the muscle groups of a high performing athlete can be recorded and used as a standard against which other lower performing athletes are compared. Based on such comparison, alterations in the sequence of muscle group movements can be made to improve the performance of the other athletes.

Yet another exemplary application and use of sensors in accordance with one or more aspects and features of the invention is in activation and control of prosthetics for amputees. Rather than providing alerts based on monitoring, control signals are provided to controllers of prosthetics for controlled actuation thereof by a person.

Other applications and uses of sensors in accordance with one or more aspects and features of the invention include gait (gluteal) training in runners; muscle rehabilitation after surgery; and lifting/carrying surveillance of heavy laborers.

Smartphone Application

Figure 59:
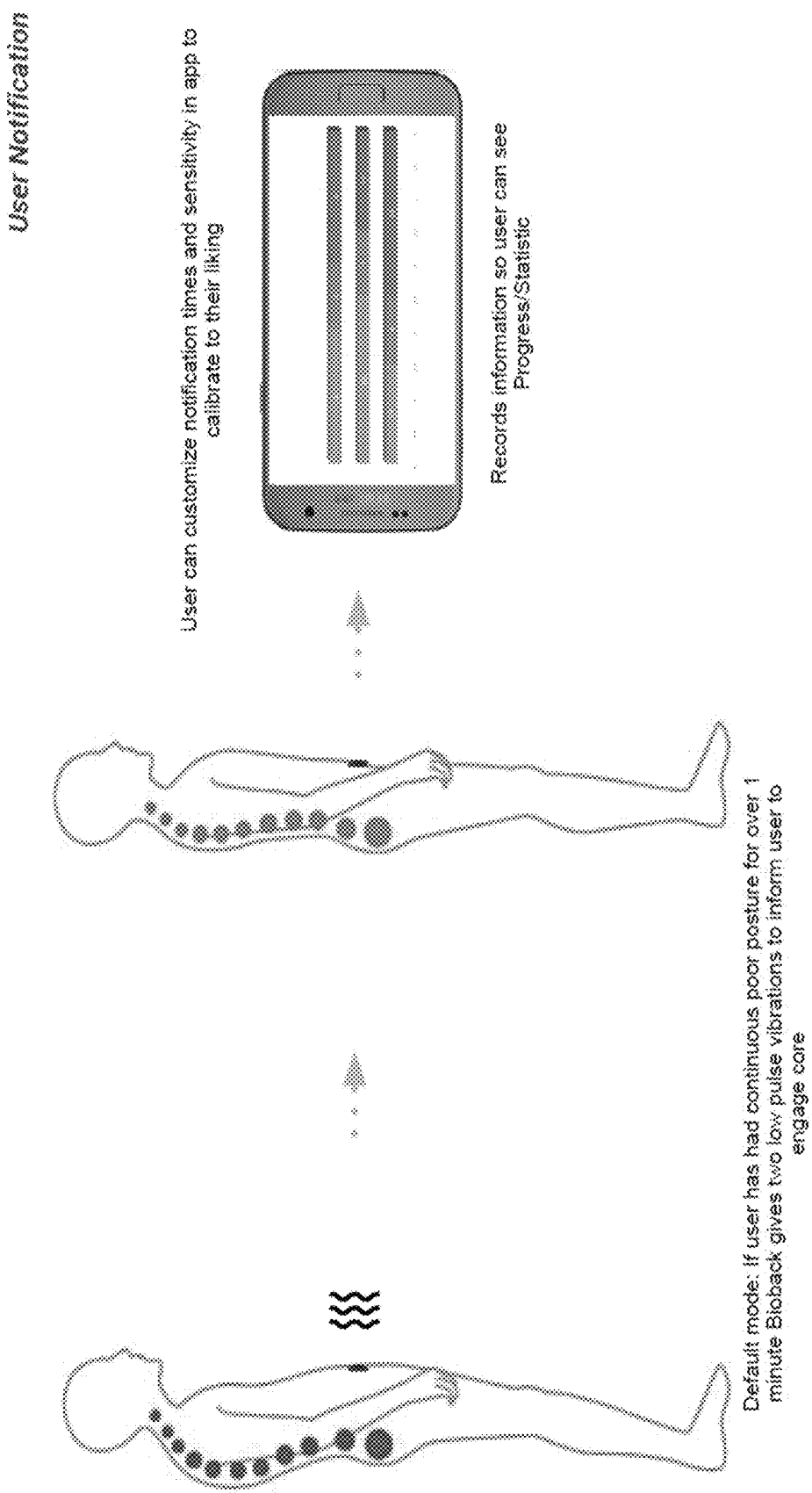
FIG. 59 is an illustration of user notification and monitoring using a smartphone.

FIG. 59 is an illustration of user notification and monitoring system using consumer electronic device in accordance with one or more aspects and features of the invention. The consumer electronic device preferably comprises a smartphone, but may be a "smart" watch such as an Apple™ watch, or may be a physical activity tracker, such as a Fitbit™ or Jawbone™ device. A sensor of the system preferably pairs or otherwise communicates with the consumer electronic device using Bluetooth™ communications, whereby data from the sensor is recorded or logged over time. Such data then may be visually displayed to a user for graphical representation of the data. For example, as seen in FIG. 59, a sensor provides vibrations in the form of two low pulse vibrations to inform the user to engage his or her core muscles (i.e., stand up straight), and the data that is acquired during such monitoring is wirelessly communicated to a smartphone where the data is recorded using an app. The app further preferably provides for customization of the settings of the sensor, including sensitivity, and customization of alert attributes, such as intensity and duration. As further seen in FIG. 59, durations of good/correct posture and bad/incorrect posture can be graphically displayed to the user for qualitative review. Progress and statistics, as well as quantitative review of the data, may also be displayed or otherwise made available for user review.

Additionally, it is contemplated that when a sensor in accordance with one or more aspects and features of the invention is paired or otherwise communications with a consumer electronic device that itself includes a component for alerting a user, including a vibrating mechanism, speaker, or both, then notification may be provided to the user through such component of the consumer electronic device, either in conjunction with such a component of the sensor or in lieu of such a component of the senor. Indeed, in implementations that include such a consumer electronic device, a senor in accordance with one or more aspects and features of the invention may not even comprise a component for providing an alert to a user.

Alternative Sensor Embodiments

FIG. 60 is a perspective view of an alternative embodiment of a sensor in accordance with one or more aspects and features of the invention, and FIG. 61 is another perspective view thereof. The sensor 1100 of FIG. 60 includes a circular sensor module 1102 and a translucent, T-shaped adhesive sensor base 1104 with electrodes 1110,1112. Electrical pathways are formed between the electrodes 1110,1112 and the sensor module 1102 by an embedded, conductive tape 1160. Audio openings 1128 are provided in a top wall of the casing of the sensor module 1102, and a charging port 1124 is located on an outwardly facing side of the sensor module 1102.

Figures 62, 63:
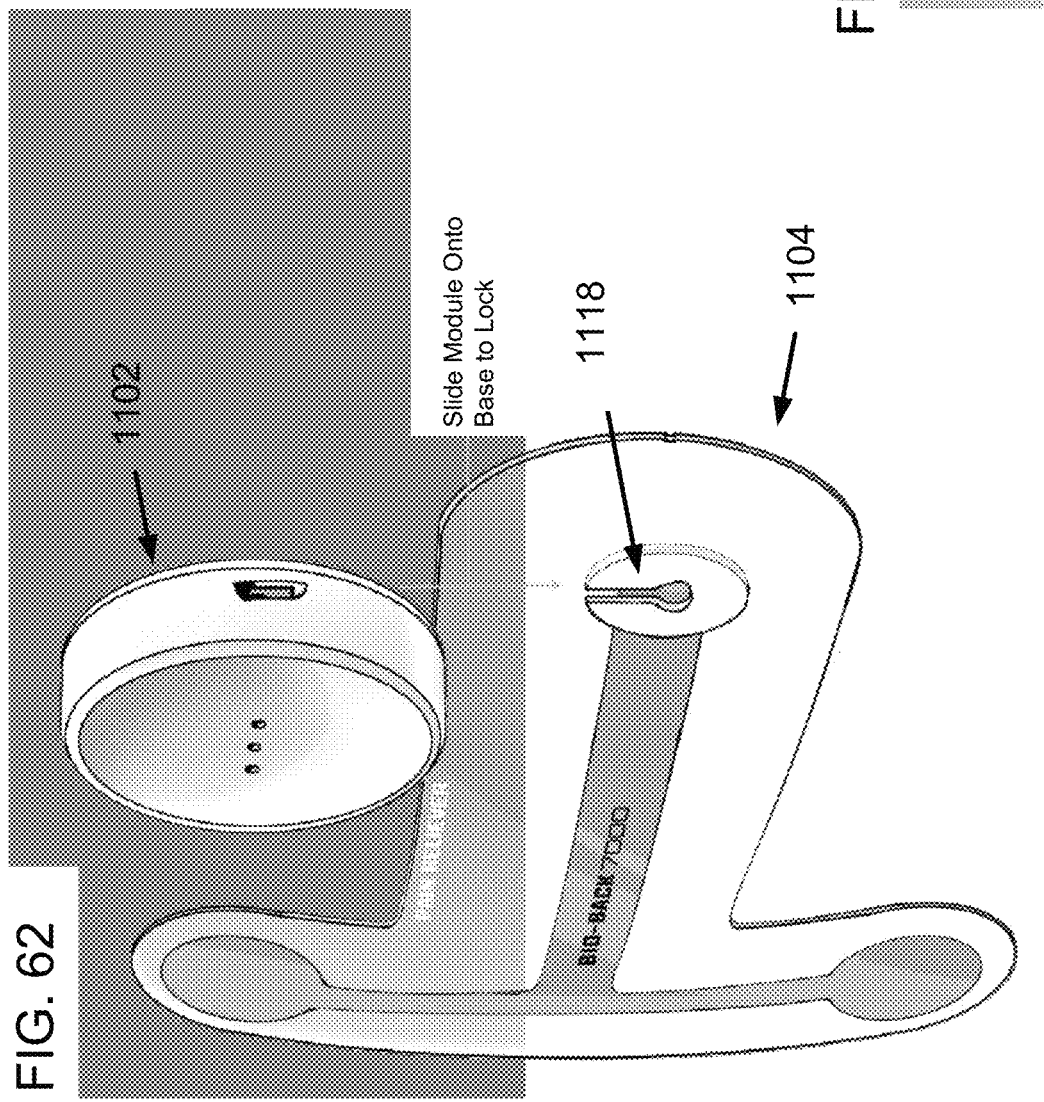
FIG. 62 is a partial exploded view of the sensor of FIG. 60.
FIG. 63 is an illustration of the sensor of FIG. 60 being worn by a person for sensing core muscles.

FIG. 62 is a partial exploded view of the sensor 1100 of FIG. 60 and illustrates the attachment structure 1118 of the sensor base 1104 having an open-ended, expandable slot for attaching the sensor module 1102 using another attachment structure (not shown) in the form of a pin that slides along the expandable slot and locks in place when the pin exits the tensioned slot and enters the center opening of the structure 1118. The pin further connects with the embedded conducted tape, which is exposed at the center opening of the structure 1118, to form the electrical communications interface between the sensor module 1102 and the sensor base 1104. FIG. 63 is an illustration of the sensor 1100 being worn by a person for measuring electrical activity of core muscles.

Figure 64:
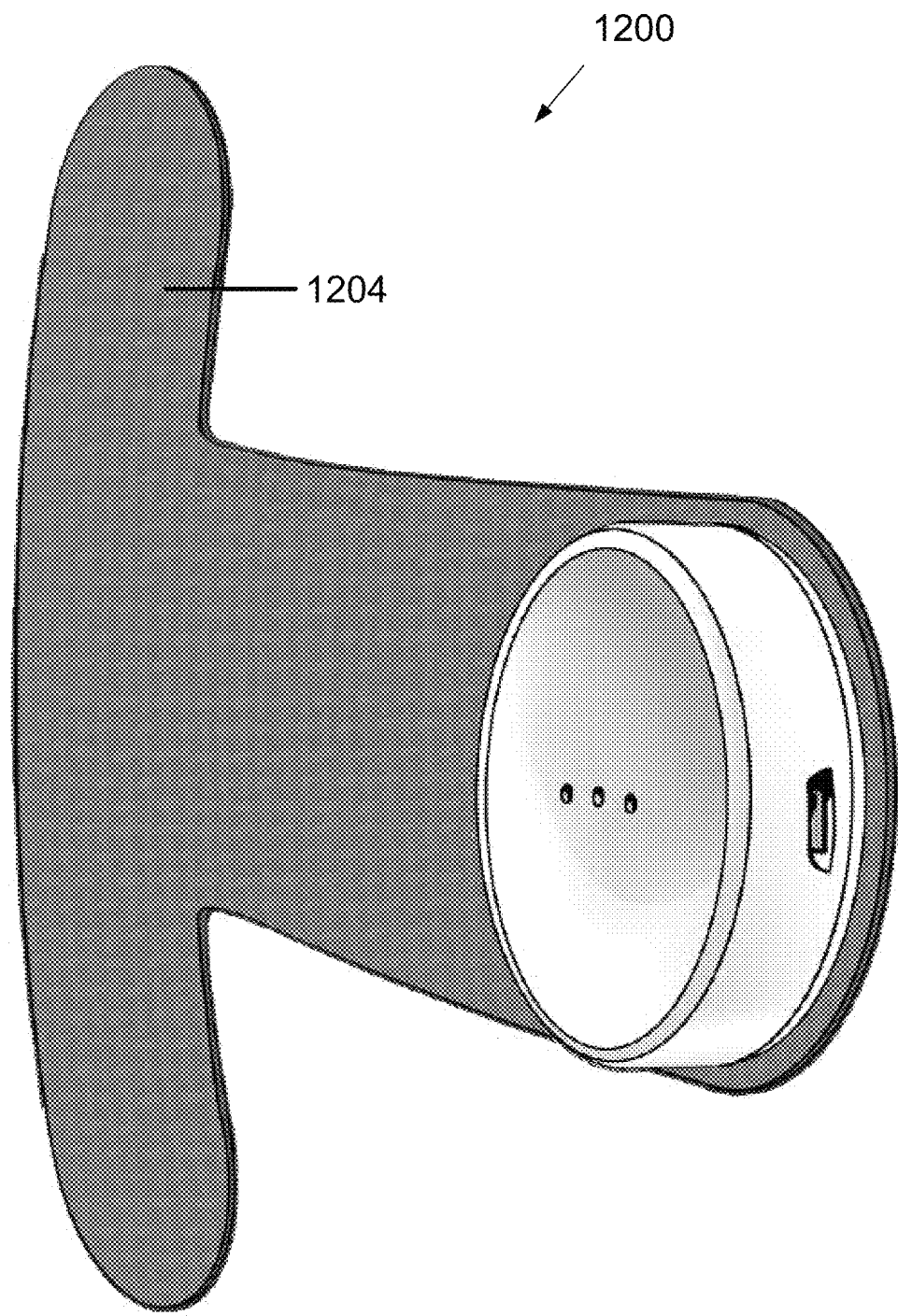
FIG. 64 is a perspective view of an alternative sensor in accordance with one or more aspects and features of the invention.

FIG. 64 is a perspective view of an alternative sensor 1200, which is similar to sensor 1100 but which comprises a sensor base 1104 comprising upper and lower layers of die-cut kinesiology tape.

Yet another embodiment of a sensor in accordance with one or more aspects and features of the invention is disclosed and described with reference to FIGS. 65-71. In particular, FIG. 65 is a perspective view of the top and the bottom of sensor 1300; FIG. 66 is a perspective view of the sensor 1300 being attached to a band of tape; FIG. 67 is a perspective view of the sensor 1300 attached to a band of tape; and FIG. 68 is a side elevational view of the sensor 1300. Sensor 1300 comprises a casing 1322, with which a clip 1370 is integrally formed and from which the clip 1370 extends along a back of the sensor 1370 so as to define a narrow spacing 1372 between a surface of the clip 1370 and a back surface of the casing 1322. The spacing 1372 is configured to receive a band of kinesiology tape therein between the clip and the casing for attaching the sensor 1300 to a person's skin. The clip 1370 includes electrodes 1310, 1312 for contacting the skin and measuring electrical activity of muscle in vicinity of the location where the sensor is attached to the person's body.

The casing 1322 further preferably contains circuitry preferably in the form of a circuit board for sensor operations (not shown, but similar to circuit board 950); a microcontroller for wireless communications (not shown); a battery for powering the sensor (not shown), which batter may be replaceable by opening at least a portion of the casing; and a component for alerting a person wearing the sensor, which preferably comprises a vibration mechanism (not shown). The sensor module 102 also comprises a light emitting component, such as an LED 1332, for indicating a level of electric charge of the battery.

For example, FIG. 69 is a perspective view illustrating an attachment location of the sensor 1300 to a person's shoulder using kinesiology tape having a footprint accommodating the person's shoulder; FIG. 70 is a perspective view illustrating an attachment location of the sensor 1300 to a person's lower back using kinesiology tape having a footprint accommodating the person's lower back; and FIG. 71 is a perspective view illustrating an attachment location of the sensor 1300 to a person's thigh using kinesiology tape having a footprint accommodating the person's thigh.

Electrode Placement

Figure 72:
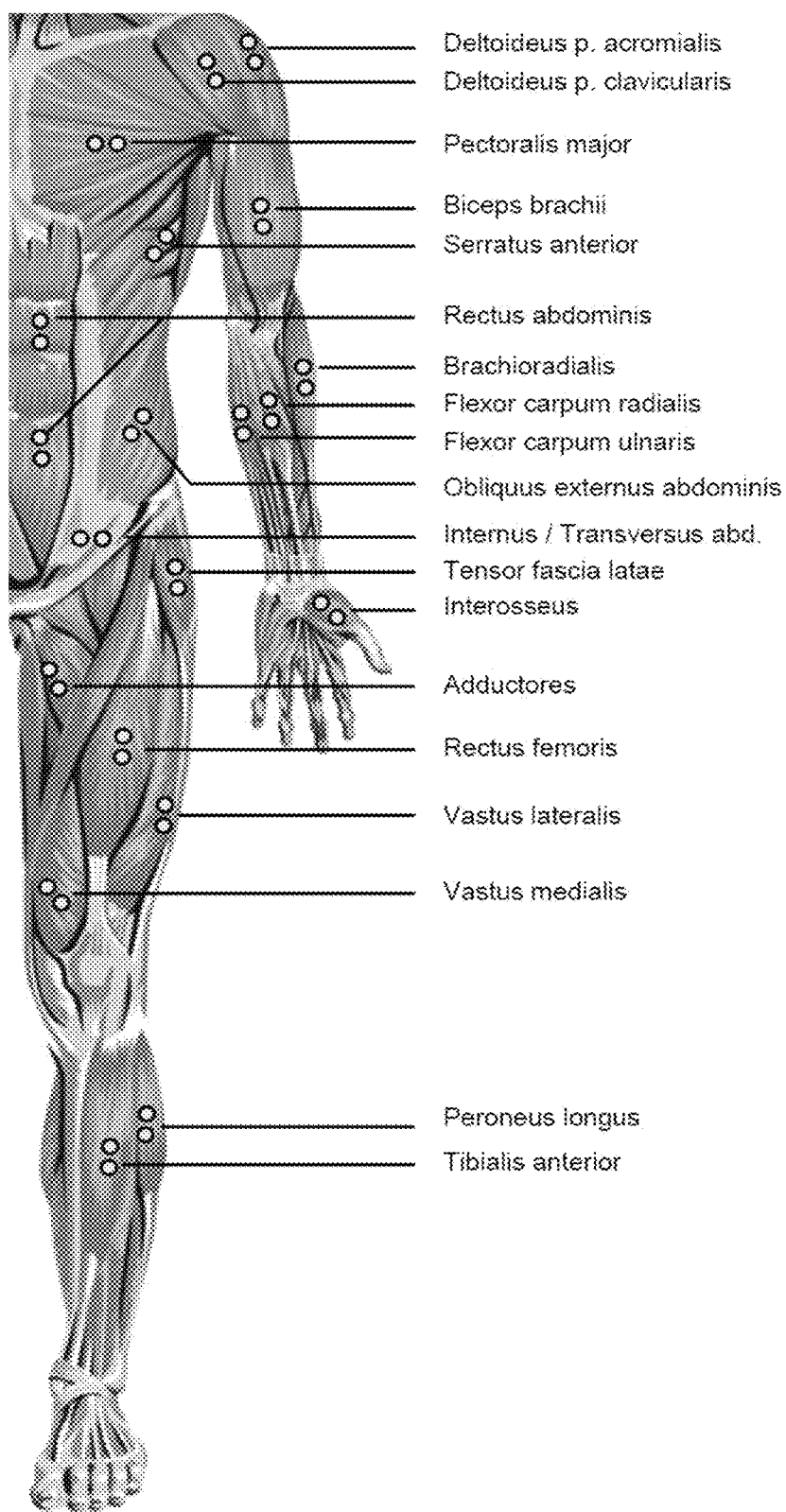
FIG. 72 is a plan view of half of a front of a human body illustrating preferred electrode pair placements for defined muscle groups.
Figure 73:
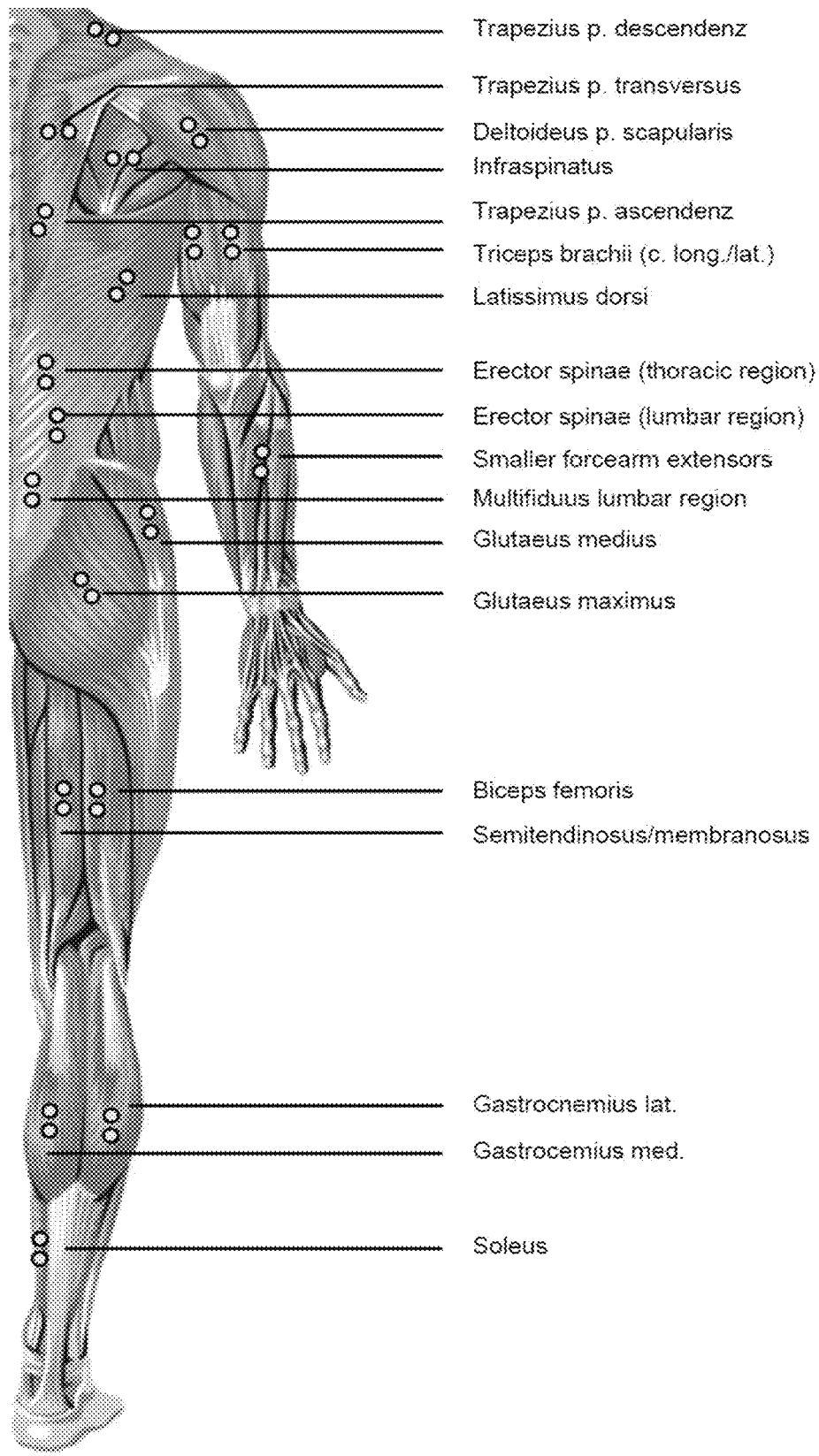
FIG. 73 is a plan view of half of a back of human body illustrating preferred electrode pair placements for defined muscle groups.

EMG surface electrodes of sensors in accordance with one or more aspects and features of the invention preferably each comprise a contact surface having a diameter of approximately 10 mm and centers that are spaced apart from one another by approximately 20 mm. Placement of the electrodes with respect to muscle groups is shown by the pairs of yellow circles marked on the rendering of a human body seen in FIGS. 72 and 73.

Based on the foregoing description, it will be readily understood by those persons skilled in the art that the present invention has broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

For example, while electro-myographic sensors have been described above in connection with preferred embodiments of the invention, sensors in accordance with one or more of the broader aspects and features of the invention may comprise sensing technologies for cardiac monitoring, sensing technologies for monitoring respiratory rhythm and volume, sensing technologies for monitoring pulse oximetry/blood oxygen saturation, sensing technologies for monitoring hear rate and breathing, sensing technologies for monitoring galvanic skin response for emotion recognition, sensing technologies for monitoring temperature, sensing technologies for monitoring humidity, sensing technologies for monitoring sound and light waves for location and movement detection, and sensing technologies for monitoring force and pressure. Any of the foregoing monitoring may be in addition to or an alternative to sensing technologies for monitoring muscular activity. In another example, the sensor base comprises a fabric article in the form of an article of clothing.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A wearable, electro-myographic sensor module, comprising:
   (a) a casing containing components comprising
      (i) circuitry for sensor operations,
      (ii) a microcontroller,
      (iii) a transceiver for wireless communications,
      (iv) a power source for powering the sensor module, and
      (v) means for alerting a person wearing the sensor module;
   (b) an attachment structure comprising recesses formed in the casing defining exposed openings in a bottom surface of the sensor module for releasable engagement therein of the sensor module with a sensor base that is attachable to a person; and
   (c) an interface comprising electrical pins arranged in electrical communication with the circuitry and extending within the recesses for electrically connecting the circuitry to electrodes of the sensor base when the sensor module is releasably engaged with the sensor base, distal ends of the pins terminating within the recesses such that the pins do not extend beyond the bottom surface of the casing;

(d) wherein the components of the sensor module are configured to measure through the interface an electrical activity of muscle that varies during contraction and relaxation and, based thereon, alert a person wearing the sensor module when an incorrect posture of the person is detected.

2. The sensor module of claim 1, wherein the power source comprises a battery.

3. The sensor module of claim 1, wherein the power source comprises a rechargeable battery.

4. The sensor module of claim 3, wherein the sensor module further comprises a charging port located in a wall of the casing.

5. The sensor module of claim 1, wherein the sensor module comprises a profile that is stored in non-transitory memory of the circuitry by which the sensor module determines transitions from relaxation to contraction of a muscle or muscle group, and a degree of contraction, and transitions from contraction to relaxation of the muscle or muscle group.

6. The sensor module of claim 1, wherein the means for alerting a person wearing the sensor module comprises a vibration mechanism.

7. The sensor module of claim 1, wherein the means for alerting a person wearing the sensor module comprises a speaker for providing an auditory alert.

8. The sensor module of claim 7, wherein the casing contains the speaker and has audio openings in a wall thereof proximate the speaker contained therein.

9. The sensor module of claim 1, further comprising a sensor base, the sensor base comprising:
   (a) a top fabric layer; and
   (b) a bottom fabric layer;
   (c) wherein electrodes of the sensor base extend through at least the bottom layer; and
   (d) wherein a sensor-module attachment structure extends through and away from the top fabric layer and is secured by the top and bottom fabric layers.

10. The sensor module of claim 9, wherein a bracket secures the sensor-module attachment structure to the electrodes.

11. The sensor module of claim 10, wherein the bracket is sandwiched between the top fabric layer and the bottom fabric layer.

12. The sensor module of claim 1, wherein the components of the sensor module are configured to measure core muscles of the person by which an incorrect posture of the person is detected.

13. The sensor module of claim 1, wherein the sensor module further comprises magnets located within the casing proximate the recesses formed in the bottom of the casing, wherein the magnets are configured to attract protuberances of the sensor base for securing the attachment of the sensor module on the sensor base when the protuberances are received within the recesses.

* * * * *